US007062049B1

(12) United States Patent
Inoue et al.

(10) Patent No.: US 7,062,049 B1
(45) Date of Patent: Jun. 13, 2006

(54) ACTIVE NOISE CONTROL SYSTEM

(75) Inventors: Toshio Inoue, Tochigi-ken (JP); Hisashi Sano, Utsunomiya (JP); Akira Takahashi, Tochigi-ken (JP); Kenichi Terai, Shijonawate (JP); Hiroyuki Hashimoto, Daito (JP); Isao Kakuhari, Ikoma (JP)

(73) Assignees: Honda Giken Kogyo Kabushiki Kaisha, Tokyo (JP); Matsushita Electric Industrial Co., Ltd., Osaka-fu (JP)

( * ) Notice: Subject to any disclaimer, the term of this patent is extended or adjusted under 35 U.S.C. 154(b) by 0 days.

(21) Appl. No.: 09/522,178

(22) Filed: Mar. 9, 2000

(30) Foreign Application Priority Data

Mar. 9, 1999 (JP) ................................ 11-061908
Mar. 29, 1999 (JP) ................................ 11-087149
Feb. 1, 2000 (JP) ............................ 2000-024095

(51) Int. Cl.
*A61F 11/06* (2006.01)
(52) U.S. Cl. ........................................ 381/71.4; 381/86
(58) Field of Classification Search ...... 381/71.1–71.4, 381/86, 56–57, 108, 71.6–71.7
See application file for complete search history.

(56) References Cited

U.S. PATENT DOCUMENTS 5,410,607 A * 4/1995 Mason et al. ................. 381/71
5,651,072 A * 7/1997 Nakao et al. .............. 381/71.2
5,692,055 A * 11/1997 Sano et al. .................... 381/71
5,701,349 A * 12/1997 Sano et al. .................... 381/71
5,734,727 A * 3/1998 Flaherty et al. ............... 381/86
5,748,748 A 5/1998 Fischer et al.
5,845,236 A * 12/1998 Jolly et al. .................. 702/195
5,850,458 A * 12/1998 Tomisawa et al. ......... 381/71.4

FOREIGN PATENT DOCUMENTS

EP 457176 * 11/1991 .................. 381/86
JP 3-54515 (A) 3/1991
JP 03-077591 U 8/1991
JP Y289758 8/1991

(Continued)

OTHER PUBLICATIONS

IEICE (The institute electronics, information and communication engineers) Active Control on Vehicle Noise Masao Ishihama, Akio Kinoshita (Oct., 1991) p. 33-37.*

(Continued)

*Primary Examiner*—Huyen Le
*Assistant Examiner*—Lun-See Lao
(74) *Attorney, Agent, or Firm*—Birch, Stewart, Kolasch & Birch, LLP

(57) ABSTRACT

An active noise control system is capable of canceling out noise in the passenger compartment of a vehicle based on low-frequency road noise. The active noise control system has a feed-forward control unit for being supplied with reference signals highly correlated to noise from a noise source and generating a noise cancellation signal which is out of phase to noise in the passenger compartment of the vehicle, and a canceling sound generating unit disposed in the passenger compartment for generating a noise canceling sound in response to the noise cancellation signal from said feed-forward control unit. The active noise control system also has microphones for generating reference signals which are positioned respectively near the base of the front seat, near the center of a roof, and within a trunk compartment, i.e., respectively at vibrational antinodes of a primary or secondary acoustic normal mode of the passenger compartment in the longitudinal direction thereof. Output signals from the microphones are supplied as the reference signals.

12 Claims, 26 Drawing Sheets

FOREIGN PATENT DOCUMENTS

| | | | | |
|---|---|---|---|---|
| JP | 04-87898 | * | 7/1992 | |
| JP | 04-087898 | U | 7/1992 | |
| JP | 05-061479 | A | 3/1993 | |
| JP | 05061479 | * | 3/1993 | ................ 381/94.3 |
| JP | A5273987 | | 10/1993 | |
| JP | 05-310389 | A | 11/1993 | |
| JP | 06-308974 | A | 11/1994 | |
| JP | 07-175487 | A | 7/1995 | |
| JP | 07-248782 | A | 9/1995 | |
| JP | 08-044375 | A | 2/1996 | |
| JP | 9-127957 | A | 5/1997 | |
| JP | 10-143166 | A | 5/1998 | |
| JP | 10-254457 | A | 9/1998 | |
| JP | 10-282966 | A | 10/1998 | |
| WO | 8802912 | | 4/1988 | |
| WO | WO 96/31872 | A1 | 10/1996 | |

OTHER PUBLICATIONS

Ishihama et al., The Institute Electronics, Information and Communication Engineers, pp. 33-37 (1991).

* cited by examiner

ACTIVE NOISE CONTROL SYSTEM

BACKGROUND OF THE INVENTION

1. Field of the Invention

The present invention relates to an active noise control system for canceling out unwanted noise in a vehicle's passenger compartment with secondary noise produced out of phase with the unwanted noise (having 180°-shifted phase with respect to the phase of the unwanted noise in the passenger compartment), and more particularly to an active noise control system for canceling out unwanted noise in a closed space such as a vehicle's passenger compartment based on low-frequency road noise (also referred to as "drumming noise") in frequencies ranging from 20 to 150 Hz which is produced due to the acoustic resonant characteristics of the closed space.

2. Description of the Related Art

Active noise control systems for attenuating drumming noise in a vehicle's passenger compartment have been based on feed-forward active control as shown in FIG. 26 of the accompanying drawings.

In FIG. 26, the conventional active noise control system has attenuated noise in a vehicle's passenger compartment 24 as follows: Suspension vibrations and vehicle body vibrations that are highly correlated to the noise in the passenger compartment are detected by sensors, and detected signals from the sensors are used as a reference signal. The reference signal is supplied to an adaptive digital filter 21 and a digital filter 22 whose transfer characteristics are made equivalent to the sound field transfer characteristics of the passenger compartment. The digital filter 22 supplies its output signal to a filter coefficient updating circuit 23 which calculates filter coefficients w1, w2, w3, . . . , wi of the adaptive digital filter 21 based on an LMS algorithm. The filter coefficients w1, w2, w3, . . . , wi calculated by the filter coefficient updating circuit 23 are set in the adaptive digital filter 21, which applies an output signal to drive a speaker 25 that functions as a secondary noise source placed in the passenger compartment 24 which serves as a sound field. The difference between a sound radiation outputted from the speaker 25 and noise in the passenger compartment 24 is detected by a microphone 26 which is provided in the passenger compartment 24 for confirming noise cancellation. An output signal from the microphone 26 is sent as an error signal to the filter coefficient updating circuit 23, which calculates filter coefficients w1, w2, w3, . . . , wi in order to eliminate the square of the error signal.

The adaptive digital filter 21, the digital filter 22, and the filter coefficient updating circuit 23 jointly make up a control means for being supplied with a signal highly correlated to a sound from a noise source as a reference signal and generating a noise canceling signal which is exactly out of phase to the noise in the passenger compartment 24. The speaker 25 serves as a canceling sound generating means for generating a noise canceling sound in response to the noise canceling signal outputted from the control means.

When the speaker 25 generates and radiates the noise canceling sound as secondary noise, the radiated secondary noise cancels out the noise in the passenger compartment 24 for thereby suppressing the noise in the passenger compartment 24.

Efforts have also been made to adjust the weight of a certain region of the vehicle body for attenuating noise generated in the passenger compartment by drumming noise.

With the conventional active noise control system, it is necessary to use a microphone for confirming noise cancellation in the passenger compartment and also a reference signal that is highly correlated to the noise in the passenger compartment and satisfies the causality.

For suppressing the noise in the passenger compartment based on low-frequency road noise, it is also necessary to obtain a reference signal that is highly correlated to the noise in the passenger compartment and satisfies the causality. However, it is very difficult to produce such a reference signal.

The difficulty arises out of the fact that the noise in the passenger compartment based on low-frequency road noise is affected more greatly by the acoustic resonant characteristics of the sound field in the vehicle body than by vibrational characteristics of the suspensions and various vehicle body regions.

Japanese laid-open patent publication No. 5-273987 discloses a conventional active noise control system having a microphone for confirming noise cancellation which is mounted on a side of the headrest of a front seat in a passenger compartment. The microphone detects noise in the vicinity of the ears of a passenger seated on the front seat to cancel noise in the passenger compartment. In the disclosed conventional active noise control system, the understanding of transfer characteristics with respect to sounds in the passenger compartment, particularly transfer functions between a speaker as a secondary noise source and the microphone for confirming noise cancellation, has an important effect on the noise cancellation capability of the system.

However, since the front seat with the microphone mounted on the side of the headrest thereof is adjustable in position, when the front seat is moved forward or backward, the position of the microphone is changed in the passenger compartment. When the microphone is changed in position, the relative position between the speaker and the microphone is also changed. As a result, the transfer function between the speaker and the microphone is varied, and the noise in the passenger compartment cannot sufficiently be attenuated.

The above problem also occurs when the angle of the backrest of the front seat is changed.

The approach to adjust the weight of a certain region of the vehicle body for attenuating drumming noise is disadvantageous in that it has to rely upon a process of trial and error and hence is tedious and time-consuming, and the attempt usually brings about an increase in the weight of the vehicle body region.

SUMMARY OF THE INVENTION

It is a primary object of the present invention to provide an active noise control system which is capable of canceling out noise in a vehicle's passenger compartment based on low-frequency road noise.

Another object of the present invention is to provide an active noise control system which is capable of easily obtaining a reference signal.

Still another object of the present invention is to provide an active noise control system which is capable of reliably obtaining a noise cancellation confirming signal.

Yet another object of the present invention is to provide an active noise control system which is capable of easily obtaining a detected noise signal.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
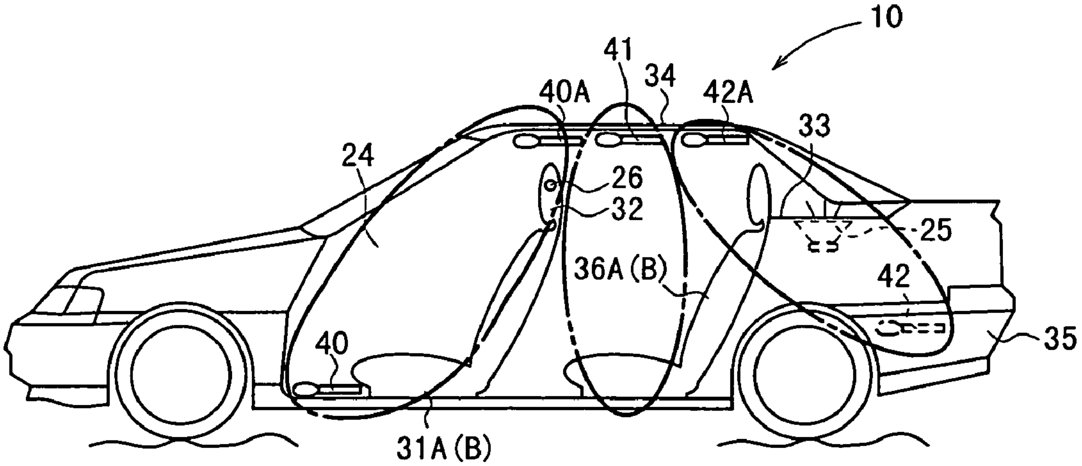
FIG. 1 is a schematic side elevational view showing the positions of microphones and a speaker in an active noise control system, which is incorporated in a sedan, according to a first embodiment of the present invention.

Like or corresponding parts are denoted by like or corresponding reference characters throughout views.

Figure 2:
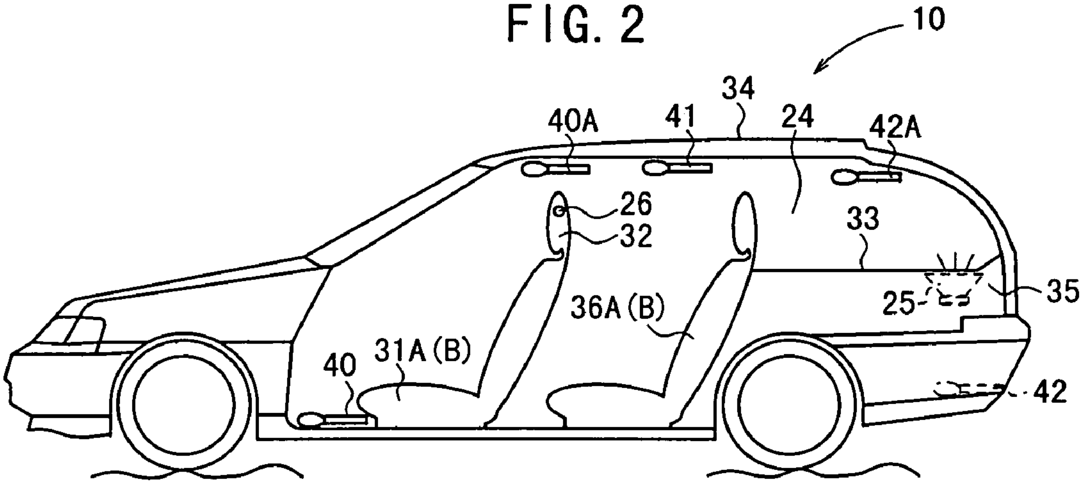
FIG. 2 is a schematic side elevational view showing the positions of the microphones and the speaker in the active noise control system, which is incorporated in a station wagon, according to the first embodiment of the present invention.

FIG. 1 schematically shows the positions of microphones and a speaker in an active noise control system according to a first embodiment of the present invention. The active noise control system according to the first embodiment of the present invention serves to cancel out noise in the passenger compartment of a vehicle 10, shown as a sedan in FIG. 1. In FIG. 1 and FIG. 2 which will be described later on, the doors of the vehicle 10 are omitted from illustration for the sake of brevity.

As shown in FIG. 1, the active noise control system according to the first embodiment of the present invention has a speaker 25 as a secondary noise source which serves as a canceling sound generating means, the speaker 25 being mounted on a rear tray 33, for example, in the vehicle 10. The active noise control system also has a microphone 26 for confirming noise cancellation which is mounted on a side of a headrest 32 of a driver seat 31A or a front passenger seat 31B of the vehicle 10. The active noise control system further has a digital filter, an adaptive digital filter, and a filter coefficient updating circuit (not shown) which are located in a certain position in the vehicle 10. The vehicle 10 has a passenger compartment 24 in which the driver seat 31A, the front passenger seat 31B, and rear passenger seats 36A, 36B are disposed.

Microphones 40, 41, 42 as sensors for generating reference signals are positioned respectively near the base of the front seat 31A or 31B, near the center of a roof 34, and within a trunk compartment 35, i.e., respectively at vibrational antinodes of an acoustic normal mode of the passenger compartment 24.

Figure 3:
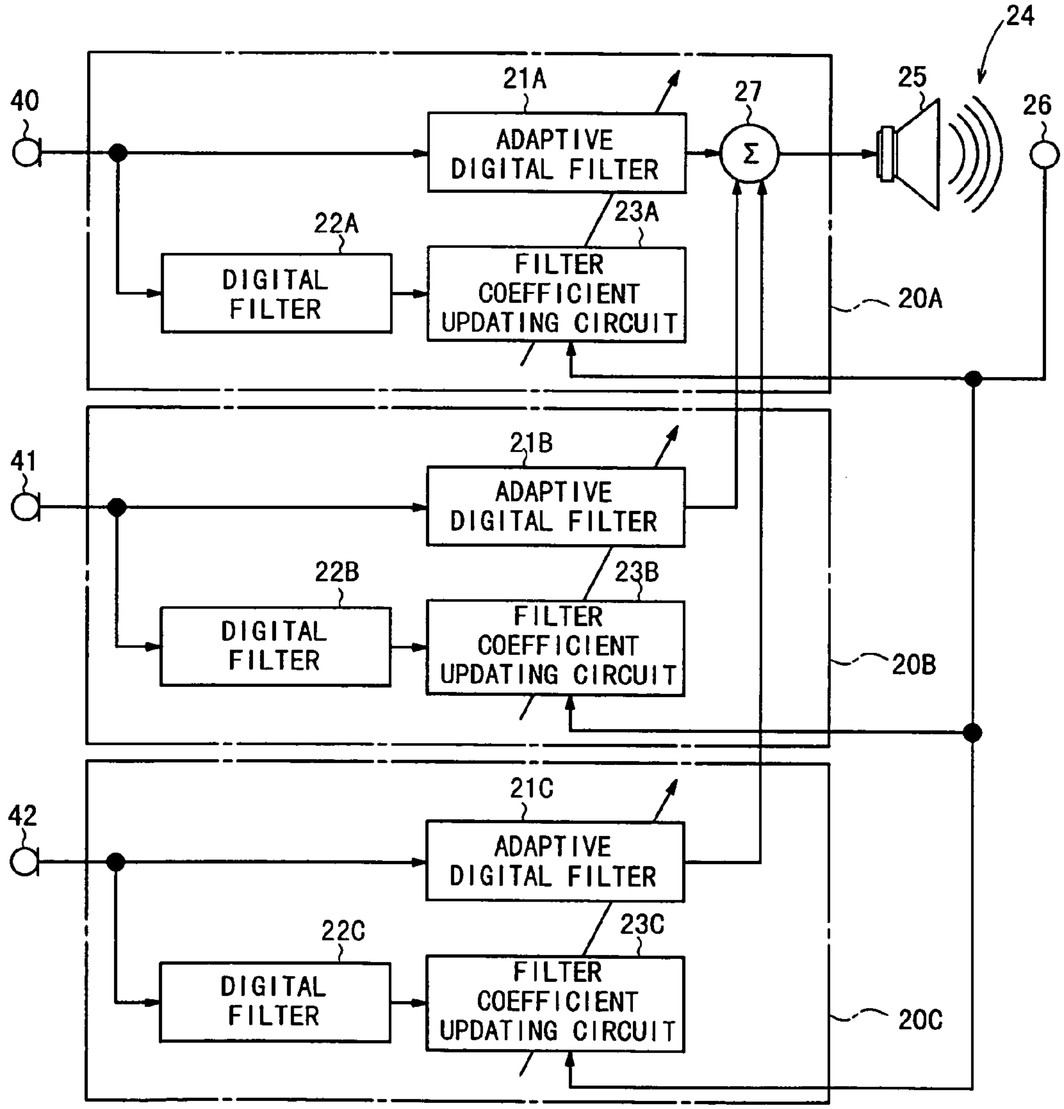
FIG. 3 is a block diagram of the active noise control system based on feed-forward control according to the first embodiment of the present invention.

As shown in FIG. 3, the active noise control system based on feed-forward control which employs the microphones 40, 41, 42 has active noise controllers 20A, 20B, 20C that are identical in structure to each other.

The active noise controller 20A operates as follows: An output signal from the microphone 40 is supplied as a reference signal to an adaptive digital filter 21A and a digital filter 22A whose transfer characteristics are made equivalent to the sound field transfer characteristics of the passenger compartment 24. The digital filter 22A supplies its output signal to a filter coefficient updating circuit 23A which calculates filter coefficients of the adaptive digital filter 21A based on an LMS algorithm. The filter coefficients calculated by the filter coefficient updating circuit 23A are set in the adaptive digital filter 21A. An output signal from the adaptive digital filter 21A and output signals from adaptive digital filters 21B, 21C (described later on) are added to each other by an adder 27. The adder 27 applies a sum signal to drive the speaker 25 placed in the passenger compartment 24 which serves as a sound field. The difference between a sound radiation outputted from the speaker 25 and noise in the passenger compartment 24 is detected by the microphone 26 which is provided in the passenger compartment 24 for confirming noise cancellation. An output signal from the microphone 26 is sent as an error signal to the filter coefficient updating circuit 23A, which calculates filter coefficients in order to eliminate the square of the error signal.

The active noise controller 20B comprises an adaptive digital filter 21B and a digital filter 22B which are supplied with an output signal from the microphone 41 as a reference signal, and a filter coefficient updating circuit 23B. Similarly, the active noise controller 20C comprises an adaptive digital filter 21C and a digital filter 22C which are supplied with an output signal from the microphone 42 as a reference signal, and a filter coefficient updating circuit 23C.

The noise in the passenger compartment 24 is canceled out by an output signal from the active noise control system, i.e., the sound radiation outputted from the speaker 25 based on the sum signal outputted from the adder 27. The digital filters 22B, 22C have transfer characteristics that are made equivalent to the sound field transfer characteristics of the passenger compartment 24.

Figure 4:
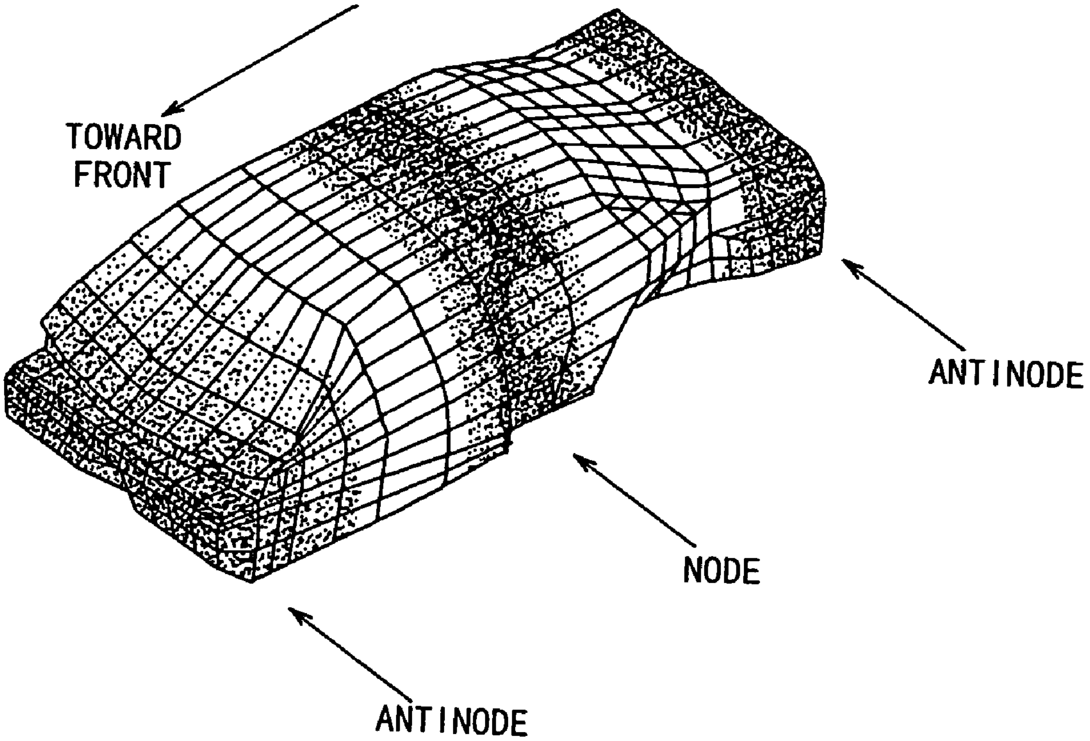
FIG. 4 is a diagram showing the result of an acoustic mode analysis of a vehicle's passenger compartment at 40 Hz according to the finite element method.
Figure 5:
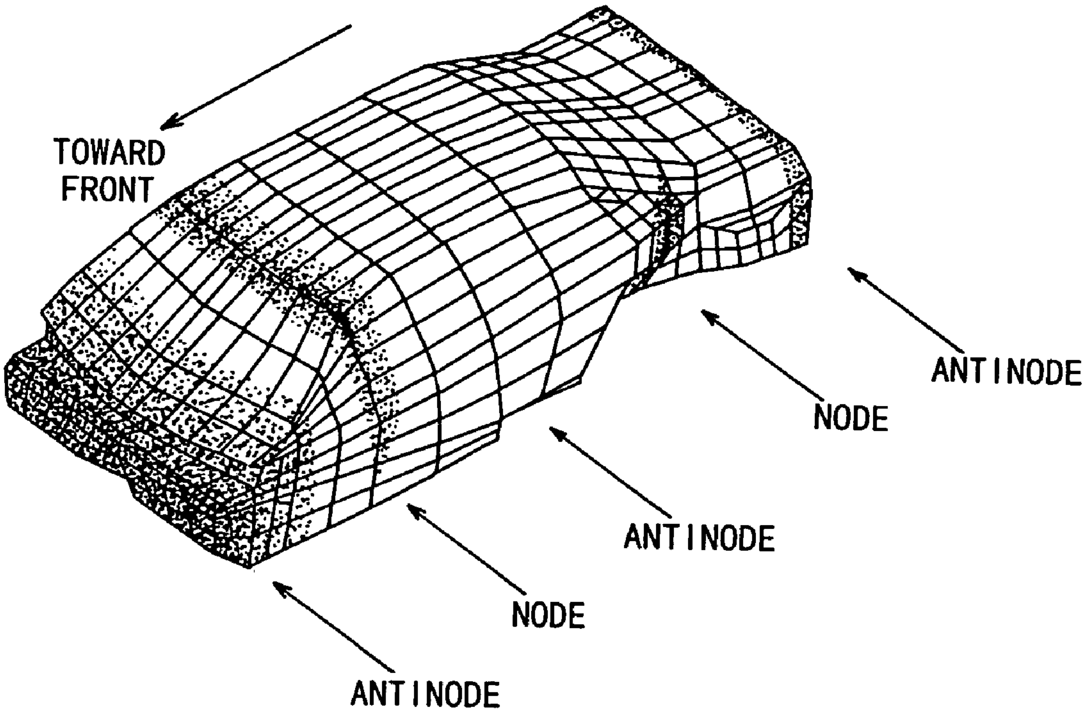
FIG. 5 is a diagram showing the result of an acoustic mode analysis of a vehicle's passenger compartment at 80 Hz according to the finite element method.

The microphones 40, 41, 42 are positioned respectively near the base of the front seat 31A or 31B, near the center of the roof 34, and within the trunk compartment 35, i.e., respectively at vibrational antinodes of the acoustic normal mode of the passenger compartment 24, for the following reasons:

An analysis of a cavity resonant mode in the passenger compartment 24 including the trunk compartment 35 according to the finite element method indicates that an acoustic normal mode of the passenger compartment 24 at low frequencies comprises a primary mode in the longitudinal direction of the vehicle at a frequency of about 40 Hz, as shown in FIG. 4, and a secondary mode in the longitudinal direction of the vehicle at a frequency of about 80 Hz, as shown in FIG. 5.

Figure 6A:
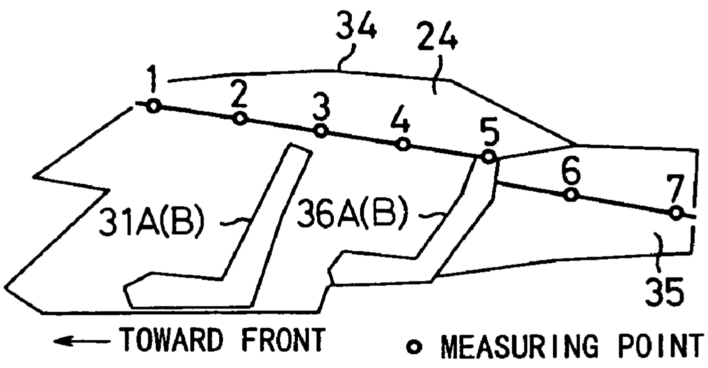
FIG. 6A is a diagram showing sound pressure measuring points in the passenger compartment of a vehicle while the vehicle is running on a rough road.

FIG. 6A shows sound pressure measuring points 1–7 disposed in the passenger compartment 24 and spaced in the longitudinal direction of the vehicle for measuring sound pressures of noise produced in the passenger compartment 24 based on road noise at a frequency of about 40 Hz, while the vehicle is running on a rough road. A distribution of noise sound pressures measured at the sound pressure measuring points 1–7 shown in FIG. 6A is shown in FIG. 6B.

Figure 7A:
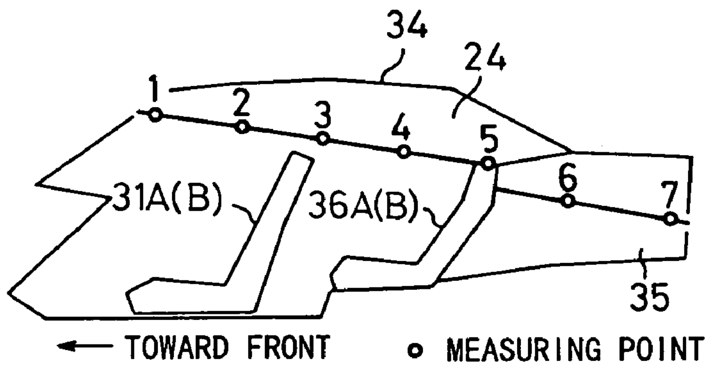
FIG. 7A is a diagram showing sound pressure measuring points in the passenger compartment of a vehicle while the vehicle is running on a rough road.

Similarly, FIG. 7A shows sound pressure measuring points 1–7 disposed in the passenger compartment 24 and spaced in the longitudinal direction of the vehicle for measuring sound pressures of noise produced in the passenger compartment 24 based on road noise at a frequency of about 80 Hz, while the vehicle is running on a rough road. A distribution of noise sound pressures measured at the sound pressure measuring points 1–7 shown in FIG. 7A is shown in FIG. 7B.

In FIGS. 6A and 7A, the vehicle has front seats 31A, 31B and rear seats 36A, 36B.

Figure 6B:
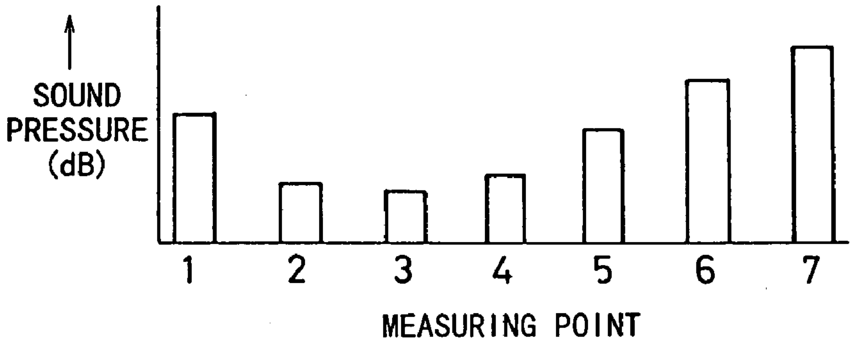
FIG. 6B is a diagram showing a distribution of measured sound pressures at 40 Hz based on low-frequency road noise at the sound pressure measuring points shown in FIG. 6A.
Figure 7B:
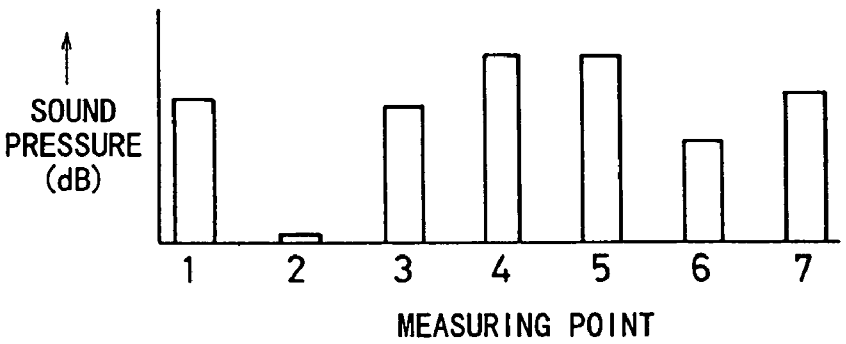
FIG. 7B is a diagram showing a distribution of measured sound pressures at 80 Hz based on low-frequency road noise at the sound pressure measuring points shown in FIG. 7A.

A comparison between FIGS. 4 and 6B and between FIGS. 5 and 7B clearly reveals that the noise produced in the passenger compartment 24 based on road noise is strongly affected by the acoustic normal mode of the passenger compartment 24.

Since the noise produced in the passenger compartment 24 based on road noise is strongly affected by the acoustic normal mode of the passenger compartment 24, coherence between the noise in the passenger compartment 24 and the error signal is high. Because the noise in the passenger compartment 24 is large, it is easy to detect a reference signal having the frequency the noise of which is to be muffled.

Though the road noise is highly random noise, inasmuch as the noise produced in the passenger compartment 24 based on road noise is strongly affected by the acoustic normal mode of the passenger compartment 24, the noise in the passenger compartment 24 is periodic, and it is not necessary to pay much attention to the causality as is the case with active noise control for periodic noise.

By positioning the microphones 40, 41, 42 respectively at vibrational antinodes of the acoustic normal mode of the passenger compartment 24 and using their output signals as reference signals, the active noise control system is capable of canceling out noise in the passenger compartment 24 based on low-frequency road noise.

Specifically, in the active noise control system according to the first embodiment, the microphones 40, 41, 42 are positioned in the passenger compartment 24 at vibrational antinodes of the primary or secondary acoustic normal mode of the passenger compartment 24. The microphones 40, 41, 42 produce respective output signals as reference signals when they detect noise at 40 Hz or 80 Hz in the passenger compartment 24, and the noise is suppressed on the basis of the reference signals. As a result, the noise at the positions of the microphones 40, 41, 42 is attenuated. Accordingly, the active noise control system is capable of suppressing not only the noise at the positions of the microphones 40, 41, 42, but also noise in a low frequency range including drumming noise in the entire passenger compartment 24.

The noise at 40 Hz and the noise 80 Hz behaves as a standing wave in the passenger compartment 24. The active noise control system according to the first embodiment operates to change the standing wave in the passenger compartment 24 in order to lower the sound pressures of the antinodes of the standing wave where the microphones 40, 41, 42 are located. In some cases, the active noise control system can cancel out the standing wave in order to suppress the noise in the entire passenger compartment 24.

Figure 8:
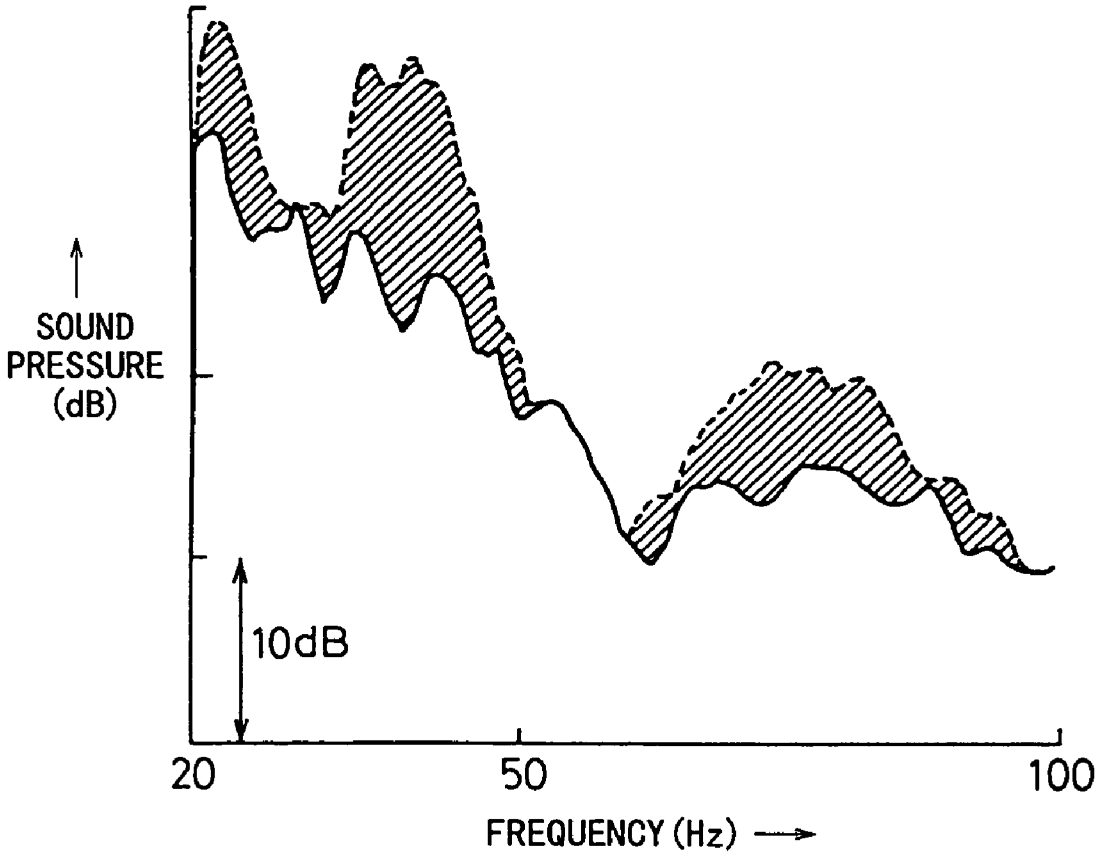
FIG. 8 is a diagram illustrative of a noise cancellation effect of the active noise control system according to the first embodiment of the present invention.

FIG. 8 illustrates a noise cancellation effect of the active noise control system for canceling noise in the passenger compartment based on low-frequency road noise by using the output signals from the microphones 40, 41, 42 as reference signals. In FIG. 8, noise which is attenuated by the active noise control system is indicated by the solid-line curve, and noise which is not attenuated by the active noise control system is indicated by the broken-line curve. The comparison between these curves clearly shows that the active noise control system is effective to cancel out the noise.

Figure 9:
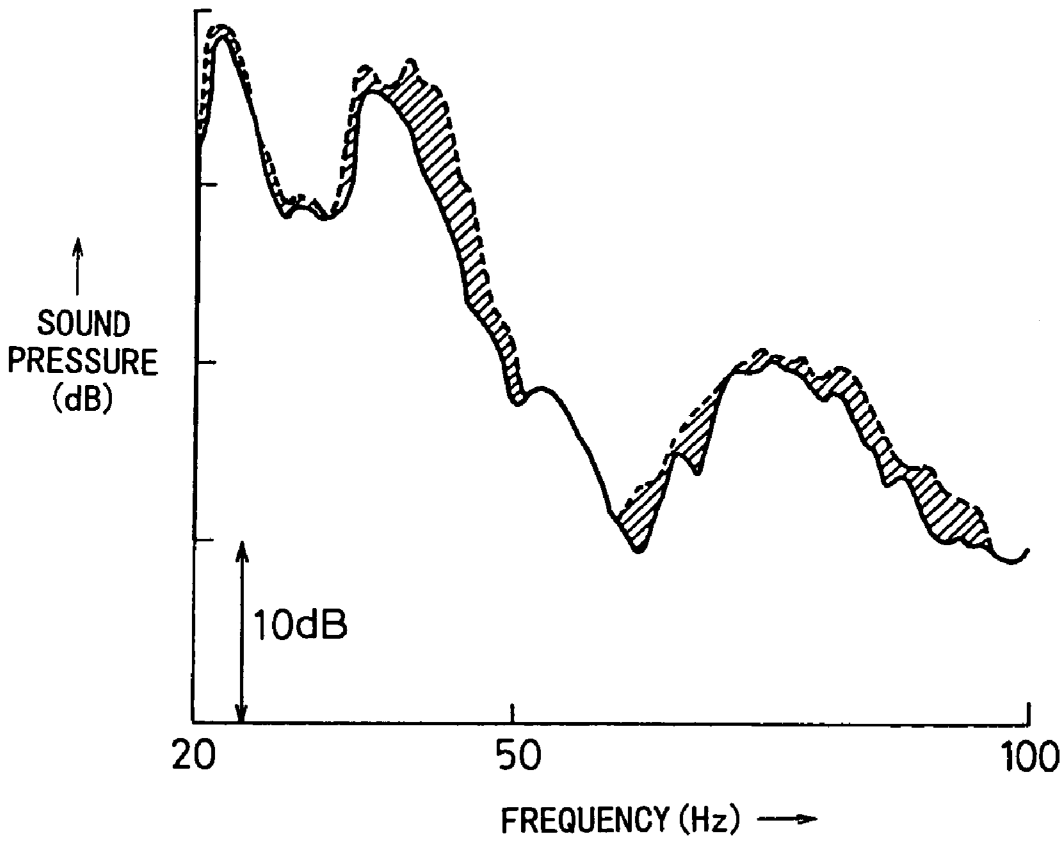
FIG. 9 is a diagram illustrative of a noise cancellation effect of a conventional active noise control system.

FIG. 9 shows a noise cancellation effect of a conventional active noise control system which uses suspension vibrations as a reference signal. In FIG. 9, noise suppressed by the conventional active noise control system is indicated by the solid-line curve, and noise which is not attenuated by the conventional active noise control system is indicated by the broken-line curve. It can be seen from the comparison between FIGS. 8 and 9 that the active noise control system according to the first embodiment is more effective to attenuate noise than the conventional active noise control system. In FIG. 9, noise indicated by the broken line curve, which is not attenuated by the active noise control system, is the same as corresponding noise in FIG. 8.

As described above, in order to cancel out noise in the passenger compartment based on road noise, it is effective to position the microphones 40, 41, 42 respectively near the base of the front seat 31A or 31B, near the center of the roof 34, and within the trunk compartment 35, as shown in FIG. 1, and use output signals from the microphones 40, 41, 42 thus positioned as reference signals.

As shown in FIG. 1, the microphone 40 may be replaced with a microphone 40A positioned near the room mirror or back on the instrument panel. The microphone 41 may be replaced with a microphone positioned near a roof rail or near a lower portion of a B pillar. The microphone 42 may be replaced with a microphone 42A positioned near the rear end of the roof of the vehicle 10. The positions of these alternative microphones correspond to antinodes of the acoustic normal mode of the passenger compartment 24. In FIG. 1, regions indicated by the dot-and-dash lines represent antinodes of the acoustic normal mode of the passenger compartment 24 at the frequencies of about 40 Hz and 80 Hz, and a region indicated by the two-dot-and-dash line represents an antinode of the acoustic normal mode of the passenger compartment 24 at the frequency of about 80 Hz.

The active noise control system according to the first embodiment as described above has three microphones for generating reference signals. However, the active noise control system may have only one microphone positioned in either one of the regions indicated by the dot-and-dash lines and the region indicated by the two-dot-and-dash line. The modified active noise control system is advantageous in that it has a smaller number of microphones.

In FIG. 1, the vehicle 10 which incorporates the active noise control system according to the first embodiment is a sedan. However, the vehicle 10 which incorporates the active noise control system according to the first embodiment may be a station wagon, as shown in FIG. 2. In the station wagon, the active noise control system has microphones 40, 41, 42 positioned as shown in FIG. 2 and is capable of canceling out noise in the passenger compartment 24 based on road noise, using output signals from the microphones 40, 41, 42 as reference signals. Those parts in FIG. 2 which are identical to those shown in FIG. 1 are denoted by identical reference characters in FIG. 1. The microphone 40 may be replaced with the microphone 40A, and the microphone 42 may be replaced with the microphone 42A.

Therefore, the principles of the present invention are applicable to vehicles of different shapes, irrespective whether they are sedans or station wagons.

As described above, the active noise control system according to the first embodiment has microphones located at respective antinodes of the acoustic normal mode of the passenger compartment and uses output signals from the microphones as reference signals for providing a large noise cancellation effect in a desired frequency range.

The active noise control system according to the first embodiment is greatly reduced in cost because the microphones are much more inexpensive than conventional acceleration sensors for detecting vibrations whose output signals are used as reference signals.

An active noise control system according to a second embodiment of the present invention will be described below.

Figure 10:
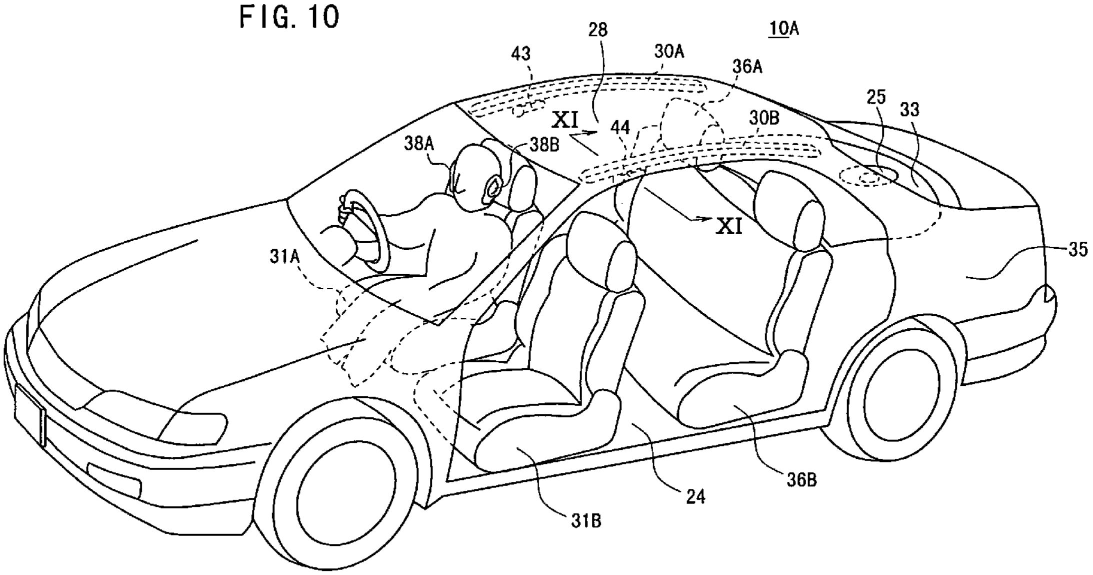
FIG. 10 is a schematic perspective view showing the positions of microphones for confirming noise cancellation and the position of a speaker as a secondary noise source of an active noise control system according to a second embodiment of the present invention.

FIG. 10 schematically shows in perspective the positions of microphones for confirming noise cancellation and the position of a speaker as a secondary noise source of the active noise control system according to the second embodiment of the present invention. The active noise control system according to the second embodiment is used to cancel out noise in the passenger compartment of a vehicle 10A which is shown as a sedan. In FIG. 10 and also FIGS. 17 and 19 (described later on), the doors of the vehicle 10A are omitted from illustration for a clearer presentation of the passenger compartment.

In the active noise control system according to the second embodiment, a speaker 25 as a secondary noise source which serves as a canceling sound generating means is mounted on a rear tray 33, for example, of the vehicle 10A, and microphones 43, 44 for confirming noise cancellation are positioned near respective left and right roof rails 30A, 30B of the vehicle 10A which confront the respective ears 38A, 38B of occupants who are seated on front seats.

Figure 12:
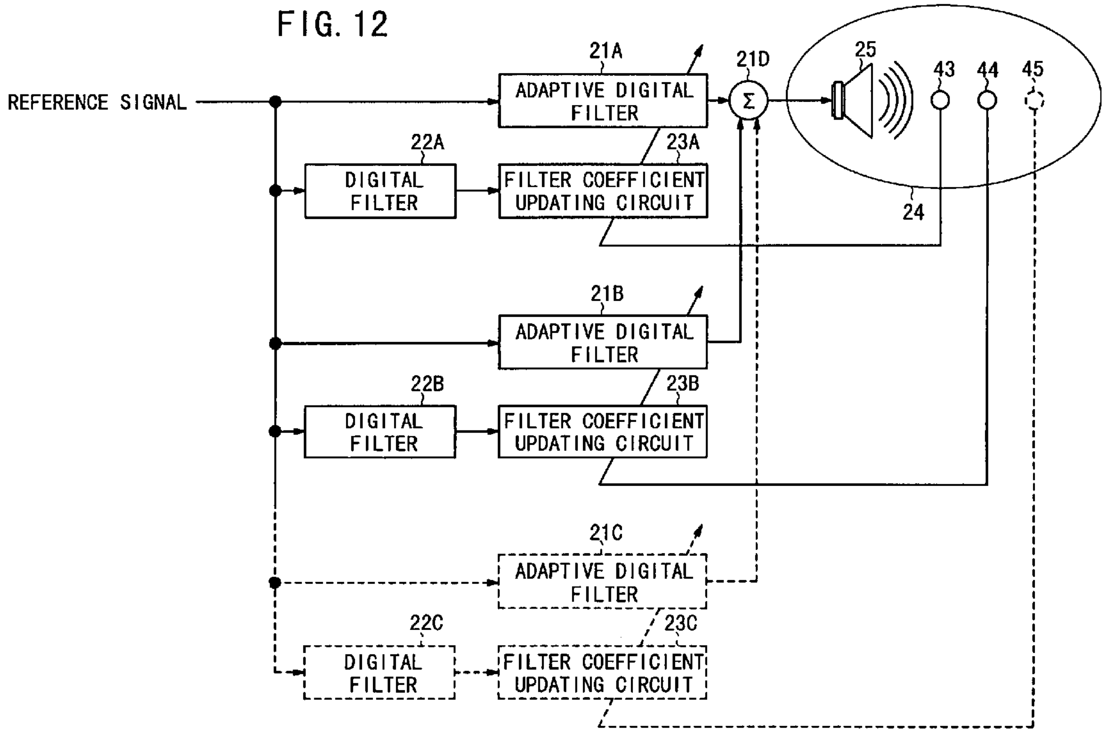
FIG. 12 is a block diagram of the active noise control system based on feed-forward control according to the second embodiment of the present invention.

As shown in FIG. 12, the active noise control system according to the second embodiment has digital filters 22A–22C, adaptive digital filters 21A–21C, filter coefficient updating circuits 23A–23C, and an adder 21D (described later on) which are located in a suitable position in the vehicle 10A. As shown in FIG. 10, the vehicle 10A has front seats 31A, 31B and rear seats 36A, 36B.

The installed position of the microphones 43, 44 will be described below with reference to FIG. 11, which shows the microphone 44 by way of example.

Figure 11:
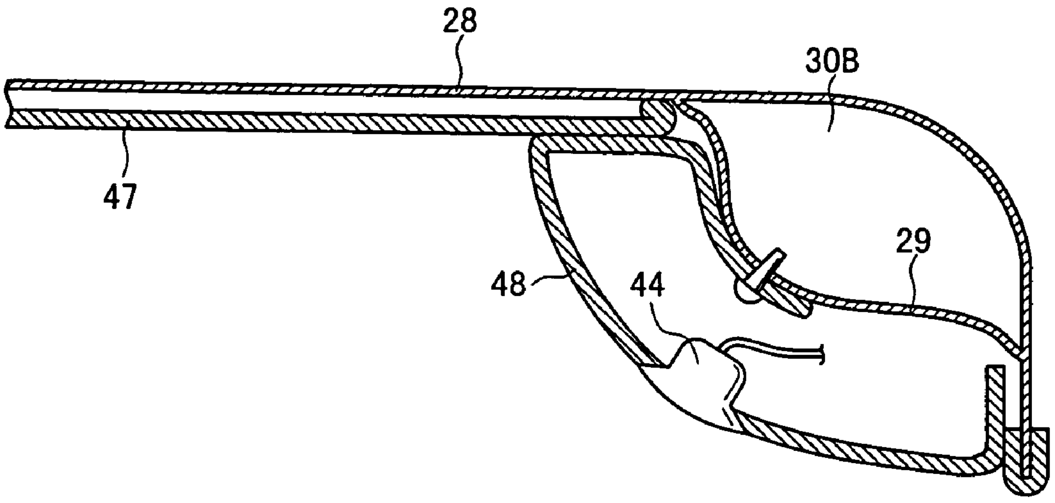
FIG. 11 is an enlarged fragmentary cross-sectional view taken along line XI—XI of FIG. 10, showing in detail one of the microphones for confirming noise cancellation of the active noise control system according to the second embodiment of the present invention.

FIG. 11 is an enlarged fragmentary cross-sectional view taken along line XI—XI of FIG. 10, showing in detail one of the microphones for confirming noise cancellation of the active noise control system.

As shown in FIG. 11, the microphone 44 is mounted on a garnish 48, for example, which is positioned in facing relationship to the left ear 38B of a passenger who is seated on the front seat 31B and near the roof rail 30B that is constructed of an outer roof panel 28 and an inner roof rail member 29 of the vehicle 10A. Similarly, the microphone 43 is mounted on a garnish, for example, which is positioned in facing relationship to the right ear 38A of the driver who is seated on the front seat 31A and near the roof rail 30A that is constructed of the outer roof panel 28 and an inner roof rail member of the vehicle 10A. A roof lining 47 is attached to the inner surface of the outer roof panel 28.

The active noise control system which includes the microphones 43, 44 is shown in block form in FIG. 12. The active noise controller shown in FIG. 12 operates as follows: A reference signal is applied to the adaptive digital filter 21A and the digital filter 22A whose transfer functions are made equivalent to the transfer functions between the speaker 25 and the microphone 43 with respect to noise in the passenger compartment 24. An output signal from the digital filter 22A is applied to the filter coefficient updating circuit 23A, and a detected noise signal produced by the microphone 43 is applied as an error signal to the filter coefficient updating circuit 23A. The filter coefficient updating circuit 23A calculates filter coefficients w1*a*, w2*a*, w3*a*, . . . , wia based on an LMS algorithm in order to substantially eliminate the square of the error signal. The calculated filter coefficients w1*a*, w2*a*, w3*a*, . . . , wia are set in the adaptive digital filter 21A.

Similarly, the reference signal is applied to the adaptive digital filter 21B and the digital filter 22B whose transfer functions are made equivalent to the transfer functions between the speaker 25 and the microphone 44 with respect to noise in the passenger compartment 24. An output signal from the digital filter 22B is applied to the filter coefficient updating circuit 23B, and a detected noise signal produced by the microphone 44 is applied as an error signal to the filter coefficient updating circuit 23B. The filter coefficient updating circuit 23B calculates filter coefficients w1*b*, w2*b*, w3*b*, . . . , wib based on an LMS algorithm in order to substantially eliminate the square of the error signal. The calculated filter coefficients w1*b*, w2*b*, w3*b*, . . . , wib are set in the adaptive digital filter 21B.

An output signal from the adaptive digital filter 21A in which the calculated filter coefficients have been set and an output signal from the adaptive digital filter 21B in which the calculated filter coefficients have been set are supplied to the adder 21D and added to each other thereby. The adder 21D applies a sum signal to drive the speaker 25 for thereby attenuating noise at the microphones 43, 44.

The microphones 43, 44 are positioned respectively near the roof rails 30A, 30B which confront the ears 38A, 38B of the occupants who are seated on the front seats in the vehicle 10A for the following reasons:

Since the microphones 43, 44 for confirming noise cancellation are positioned respectively near the roof rails 30A, 30B which confront the ears 38A, 38B of the occupants who are seated on the front seats in the vehicle 10A, the microphones 43, 44 are fixed in their relative positions, and hence the speaker 25 and the microphones 43, 44 are also fixed in their relative positions. The transfer function between speaker 25 and the microphones 43, 44 with respect to noise in the passenger compartment 24 is not varied even when the front seats are changed in position.

Figures 13A, 13B:
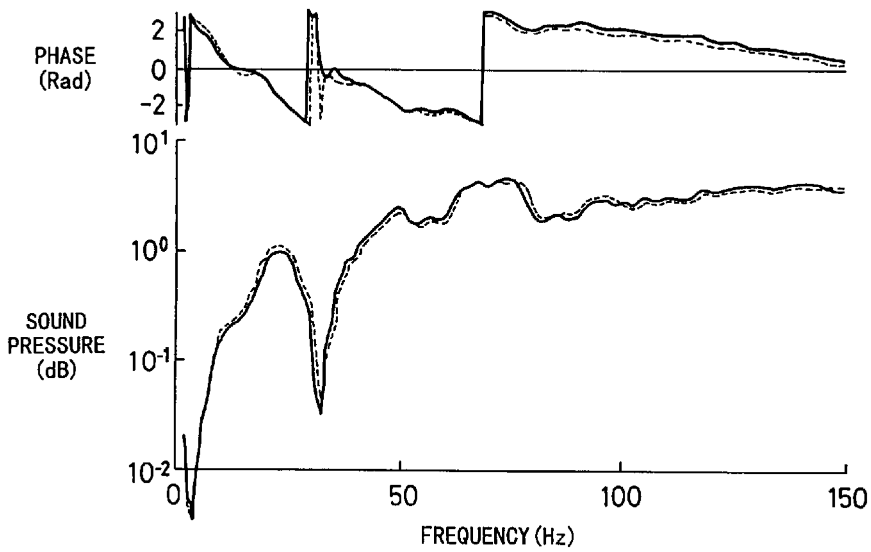
FIG. 13A is a diagram showing transfer functions (based on phase) from the speaker of the active noise control system according to the second embodiment of the present invention.
FIG. 13B is a diagram showing transfer characteristics (based on sound pressure level) from the speaker of the active noise control system according to the second embodiment of the present invention.

The transfer characteristics with respect to noise in the passenger compartment from the speaker 25 to positions near the roof rails 30A, 30B which confront the ears 38A, 38B of the occupants who are seated on the front seats, and the transfer characteristics with respect to noise in the passenger compartment from the speaker 25 to positions near the ears 38A, 38B of the occupants who are seated on the front seats are indicated respectively by the solid- and broken-line curves in FIGS. 13A and 13B, and are in substantial agreement with each other at almost all frequencies in a frequency range from 0 to 150 Hz. In FIGS. 13A and 13B, the solid-line curves represent the transfer characteristics with respect to noise in the passenger compartment from the speaker 25 to a position near the roof rails 30A, 30B which confront the ears 38A, 38B of the driver who is seated on the front seat 31A, and the broken-line curves represent the transfer characteristics with respect to noise in the passenger compartment from the speaker 25 to a position near the ears 38A, 38B of the driver who is seated on the front seat 31A. Specifically, FIG. 13A shows phase vs. frequency characteristics, and FIG. 13B shows amplitude vs. frequency characteristics. These characteristics are plotted based on data measured immediately before the vehicle runs. The illustrated transfer characteristics also hold true for the positions of the ears of the passenger who is seated on the front seat 31B.

Figure 14:
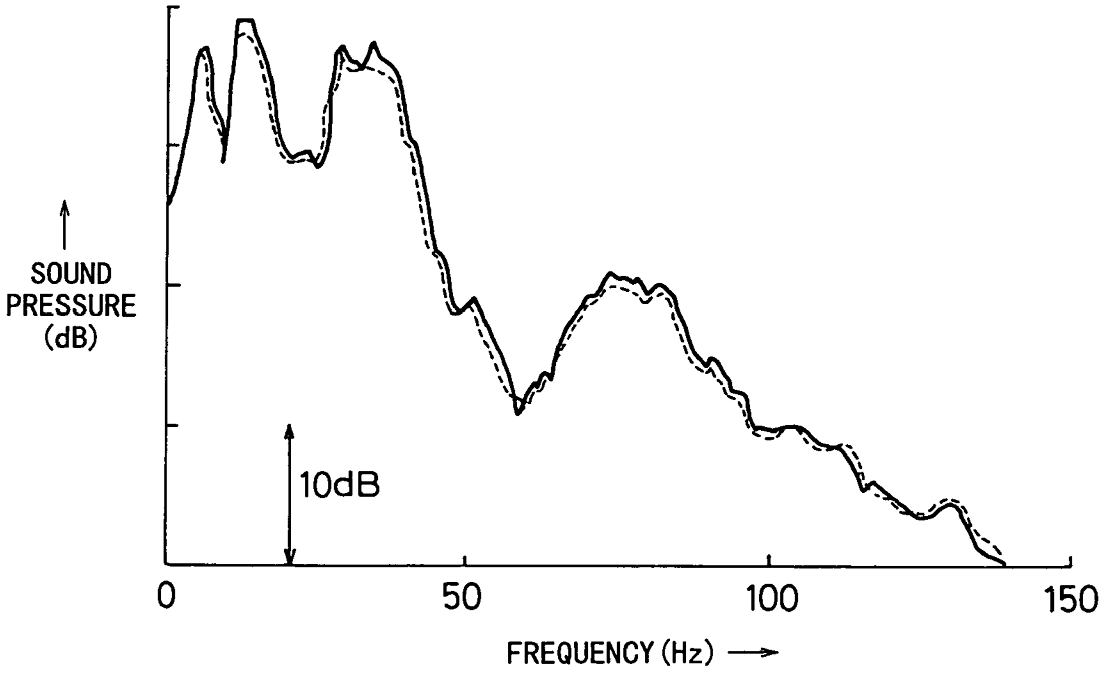
FIG. 14 is a diagram showing a spectrum of sounds in the passenger compartment of a vehicle, while it is running, incorporating the active noise control system according to the second embodiment of the present invention.

Sound pressure levels of noise in the passenger compartment from the speaker 25 to positions near the roof rails 30A, 30B which confront the ears 38A, 38B of the occupants who are seated on the front seats while the vehicle 10A is running, and sound pressure levels of noise in the passenger compartment from the speaker 25 to positions near the ears 38A, 38B of the occupants who are seated on the front seats while the vehicle 10A is running are indicated respectively by the solid- and broken-line curves in FIG. 14. There is essentially no difference between the sound pressure levels represented by these solid- and broken-line curves at each of 40 Hz and 80 Hz. In FIG. 14, the solid-line curve represents the sound pressure levels of noise in the passenger compartment from the speaker 25 to positions near the roof rails 30A, 30B which confront the ears 38A, 38B of the occupants who are seated on the front seats, and the broken-line curve represents the sound pressure levels of noise in the passenger compartment from the speaker 25 to positions near the ears 38A, 38B of the occupants who are seated on the front seats.

As described above, since the transfer characteristics with respect to noise in the passenger compartment from the speaker 25 to positions near the roof rails 30A, 30B which confront the ears 38A, 38B of the occupants who are seated on the front seats, and the transfer characteristics with respect to noise in the passenger compartment from the speaker 25 to positions near the ears 38A, 38B of the occupants who are seated on the front seats are in substantial agreement with each other, and the sound pressure levels of noise in the passenger compartment from the speaker 25 to positions near the roof rails 30A, 30B which confront the ears 38A, 38B of the occupants who are seated on the front seats, and the sound pressure level of noise in the passenger compartment from the speaker 25 to positions near the ears 38A, 38B of the occupants who are seated on the front seats are in substantial agreement with each other, the microphones 43, 44 are positioned respectively near the roof rails 30A, 30B which confront the ears 38A, 38B of the occupants who are seated on the front seats in the vehicle 10A.

An analysis of a cavity resonant mode in the passenger compartment 24 including the trunk compartment 35 according to the finite element method indicates that an acoustic normal mode of the passenger compartment 24 at low frequencies comprises a primary mode in the longitudinal direction of the vehicle at a frequency of about 40 Hz, as shown in FIG. 4, and a secondary mode in the longitudinal direction of the vehicle at a frequency of about 80 Hz, as shown in FIG. 5.

FIG. 6A shows sound pressure measuring points 1–7 disposed in the passenger compartment 24 and spaced in the longitudinal direction of the vehicle for measuring sound pressures of noise produced in the passenger compartment 24 based on road noise at a frequency of about 40 Hz, while the vehicle is running on a rough road. A distribution of noise sound pressures measured at the sound pressure measuring points 1–7 shown in FIG. 6A is shown in FIG. 6B.

Similarly, FIG. 7A shows sound pressure measuring points 1–7 disposed in the passenger compartment 24 and spaced in the longitudinal direction of the vehicle for measuring sound pressures of noise produced in the passenger compartment 24 based on road noise at a frequency of about 80 Hz, while the vehicle is running on a rough road. A distribution of noise sound pressures measured at the sound pressure measuring points 1–7 shown in FIG. 7A is shown in FIG. 7B.

In FIGS. 6A and 7A, the vehicle has front seats 31A, 31B and rear seats 36A, 36B.

A comparison between FIGS. 4 and 6B and between FIGS. 5 and 7B clearly reveals that the noise produced in the passenger compartment 24 based on road noise is strongly affected by the acoustic normal mode of the passenger compartment 24. This holds true for vehicles of different shapes, irrespective whether they are sedans or station wagons.

While low-frequency sounds in the passenger compartment undergo large sound pressure variations in the longitudinal direction of the passenger compartment 24, i.e., the direction in which the vehicle runs, they exhibit a relatively uniform sound pressure distribution in lateral and vertical directions of the passenger compartment 24. This is the basis for the reasons why the transfer characteristics with respect to noise in the passenger compartment from the speaker 25 to positions near the roof rails 30A, 30B which confront the ears 38A, 38B of the occupants who are seated on the front seats, and the transfer characteristics with respect to noise in the passenger compartment from the speaker 25 to positions near the ears 38A, 38B of the occupants who are seated on the front seats are in substantial agreement with each other at almost all frequencies, and there is no substantial difference between the sound pressure of sounds in the passenger compartment from the speaker 25 to positions near the roof rails 30A, 30B which confront the ears 38A, 38B of the occupants who are seated on the front seats while the vehicle is running, and the sound pressure of sounds in the passenger compartment from the speaker 25 to positions near the ears 38A, 38B of the occupants who are seated on the front seats while the vehicle is running. Consequently, noise in the vicinity of the ears of the occupants seated on the front seats 31A, 31B is suppressed.

Inasmuch as the microphones 43, 44 for confirming noise cancellation are positioned near the roof rails 30A, 30B facing the ears of the occupants seated on the front seats and output signals from the microphones 43, 44 are used as error signals, the active noise control system according to the second embodiment is capable of effectively canceling out noise in the passenger compartment based on low-frequency road noise.

Figure 15:
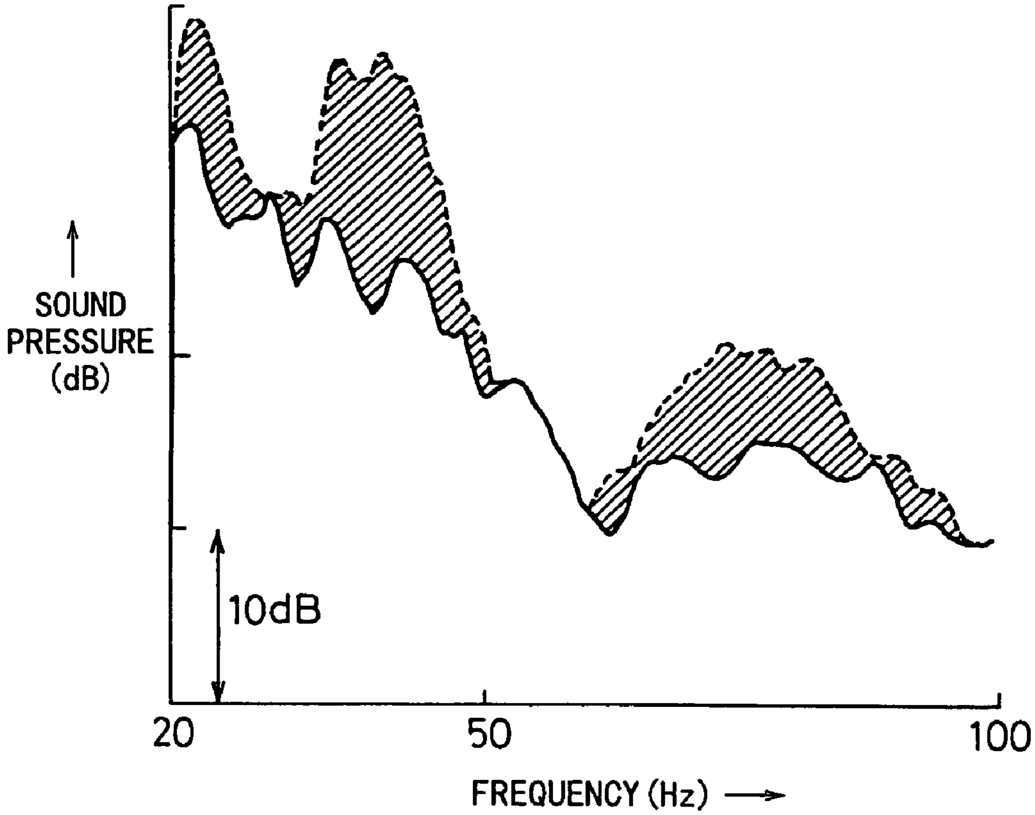
FIG. 15 is a diagram illustrative of a noise cancellation effect at the positions of the microphones of the active noise control system according to the second embodiment of the present invention.
Figure 16:
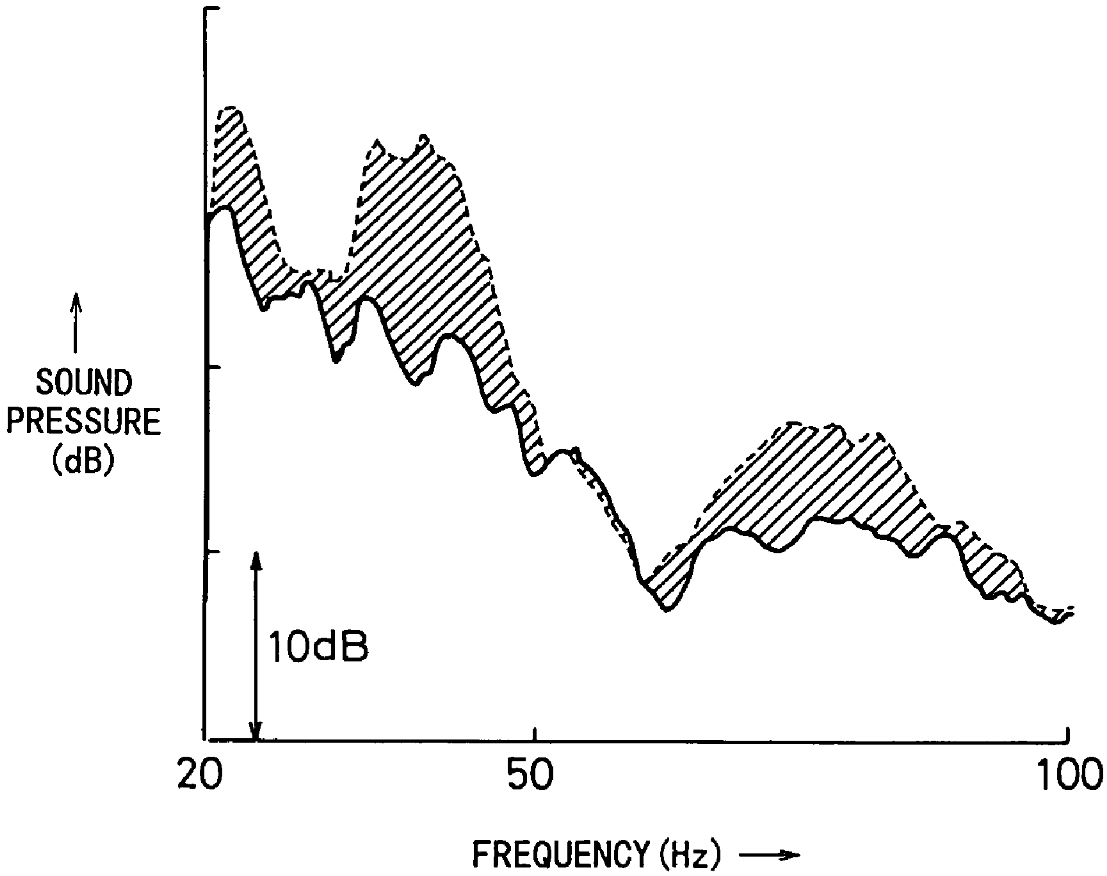
FIG. 16 is a diagram illustrative of a noise cancellation effect at the positions of the ears of a passenger in the vehicle incorporating the active noise control system according to the second embodiment of the present invention.

Because the microphones 43, 44 for confirming noise cancellation are positioned near the roof rails 30A, 30B facing the ears of the occupants seated on the front seats in the vehicle 10A, the positions of the microphones 43, 44 are fixed, and the heads of the driver and the passenger who are seated on the front seats are disposed between the microphones 43, 44, it is possible to provide a wide noise cancellation area in lateral directions at the height of the heads, i.e., in lateral directions perpendicularly to the direction in which the vehicle travels. FIG. 15 shows a noise cancellation effect at the positions of the microphones 43, 44 for confirming noise cancellation. In FIG. 15, the solid-line curve represents sound pressures measured at different frequencies when the active noise control system is in operation, and the broken-line curve represents sound pressures measured at different frequencies when the active noise control system is not in operation. FIG. 16 shows a noise cancellation effect at the positions near the ears of an occupant seated on a front seat. In FIG. 16, the solid-line curve represents sound pressures measured at different frequencies when the active noise control system is in operation, and the broken-line curve represents sound pressures measured at different frequencies when the active noise control system is not in operation. It can be seen from FIGS. 15 and 16 that a large noise cancellation effect is provided in a frequency range close to 40 Hz and a frequency range close to 80 Hz.

Figure 17:
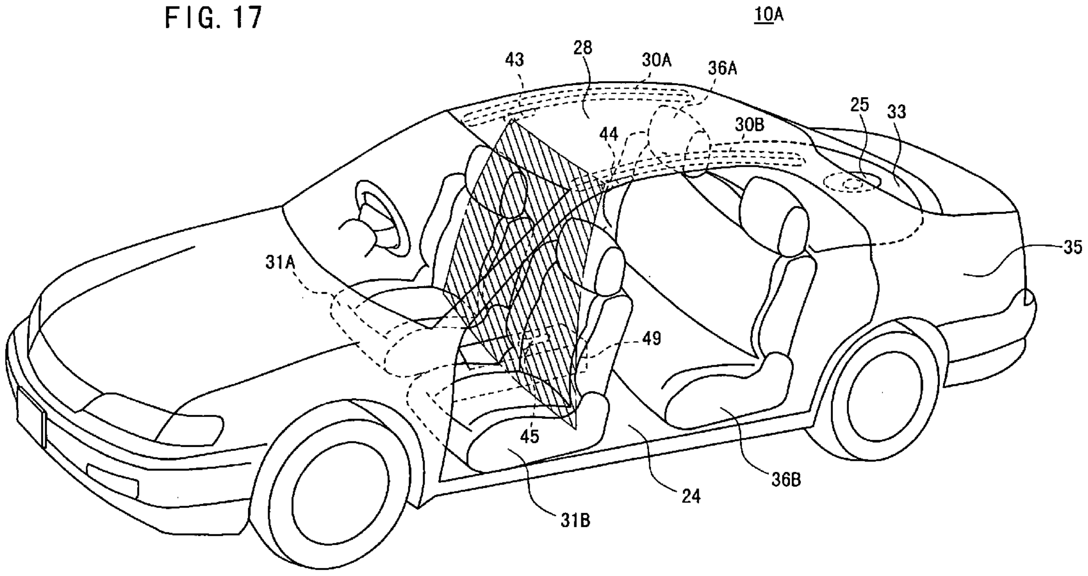
FIG. 17 is a schematic perspective view showing the position of another microphone for confirming noise cancellation of the active noise control system according to the second embodiment of the present invention.

FIG. 17 schematically shows in perspective another microphone 45 for confirming noise cancellation near a central console 49, e.g., at an armrest of the right front seat, in addition to the positions of the microphones 43, 44 for confirming noise cancellation.

With the microphone 45 added, the active noise control system additionally includes, as shown in FIG. 12, an adaptive digital filter 21C, a digital filter 22C whose transfer functions are made equivalent to the transfer functions between the speaker 25 and the microphone 45 with respect to noise in the passenger compartment 24, and a filter coefficient updating circuit 23C. The filter coefficient updating circuit 23C is supplied with an output signal from the digital filter 22C and an error signal from the microphone 45, and calculates filter coefficients w1*c*, w2*c*, w3*c*, . . . , wic based on an LMS algorithm in order to substantially eliminate the square of the error signal. The calculated filter coefficients w1*c*, w2*c*, w3*c*, . . . , wic are set in the adaptive digital filter 21C. An output signal from the adaptive digital filter 21C is supplied to the adder 21D, which adds the output signals from the adaptive digital filters 21A, 21B, 21C. A sum signal from the adder 21D is applied to drive the speaker 25 to cancel out noise in the passenger compartment 24.

Specifically, noise in a plane formed between the microphones 43, 44, 45 and shown hatched in FIG. 17 is canceled out.

Figure 18:
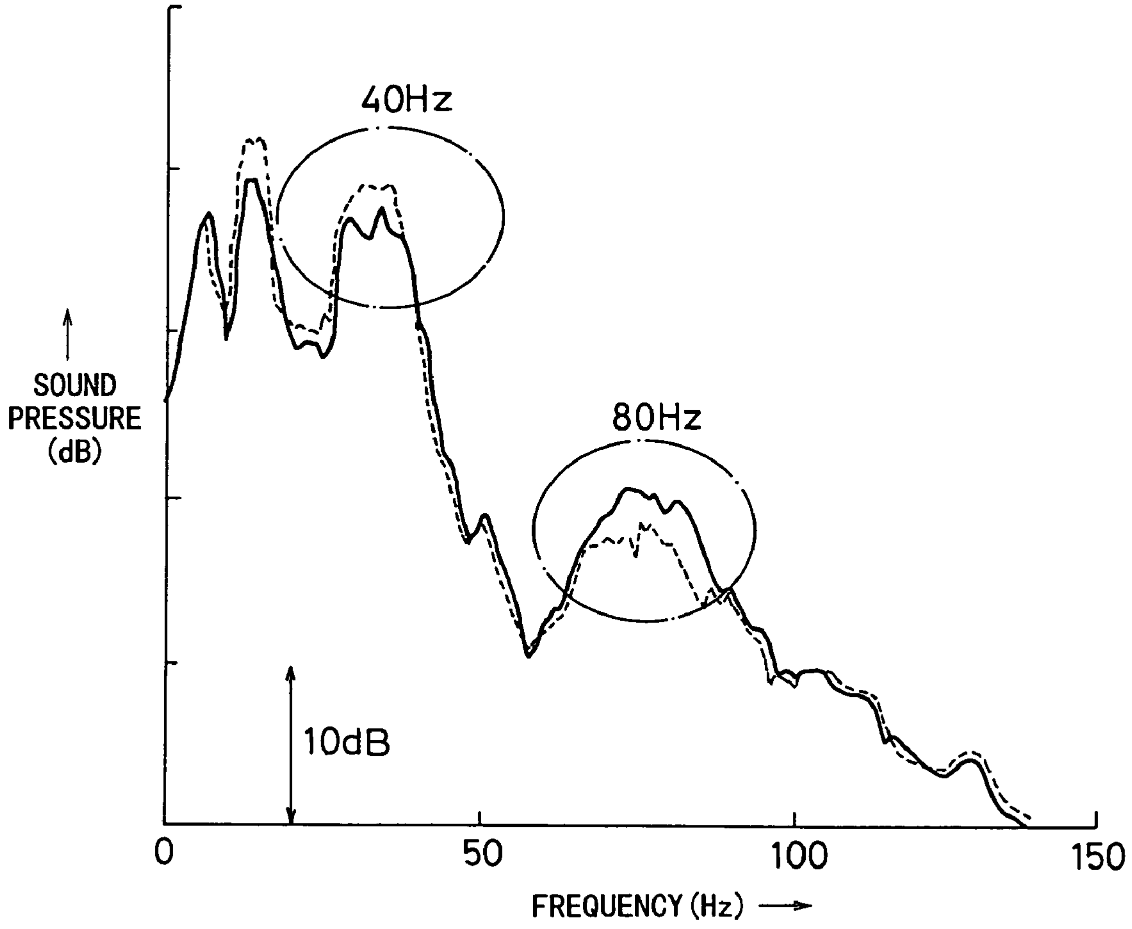
FIG. 18 is a diagram showing a spectrum of sound pressures in the passenger compartment at the positions of the ears of a passenger in the vehicle, while it is running, incorporating the active noise control system according to the second embodiment of the present invention.

FIG. 18 shows a comparison between the sound pressure levels (solid-line curve) of noise in the passenger compartment at a position near the ear, on the window side (outer side), of an occupant seated on a front seat and the sound pressure levels (broken-line curve) of noise in the passenger compartment at a position near the ear on the inner side of the passenger. It can be seen from FIG. 18 that the sound pressure level of noise at 40 Hz in the passenger compartment at the position near the ear on the inner side of the passenger is higher, and the sound pressure level of noise at 80 Hz in the passenger compartment at the position near the ear on the window side of the passenger is higher.

Figure 19:
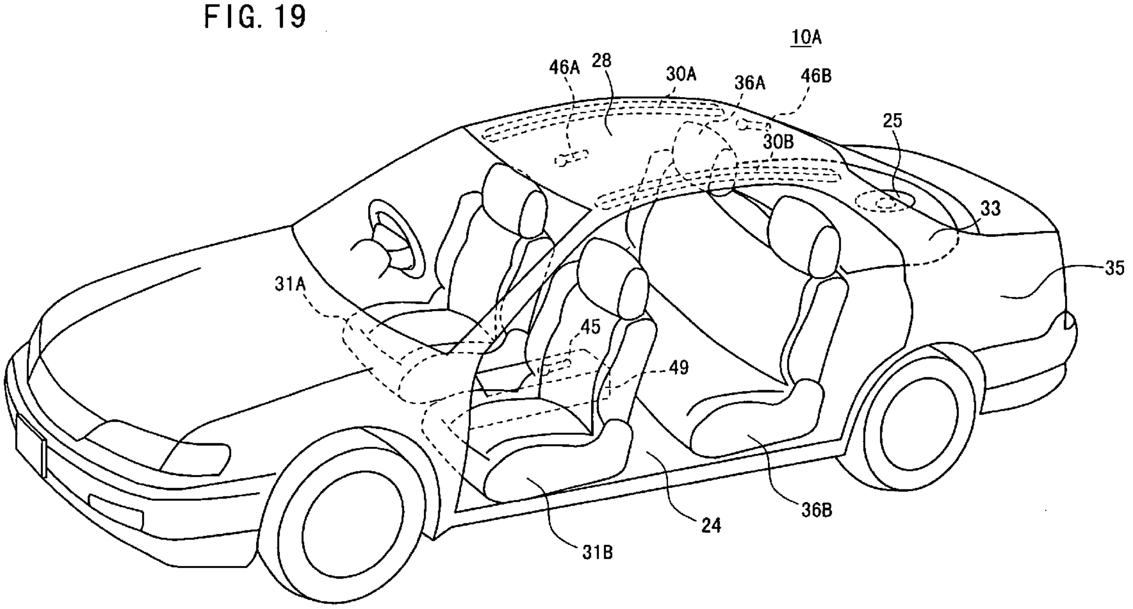
FIG. 19 is a schematic perspective view showing the position of still other microphones for confirming noise cancellation of the active noise control system according to the second embodiment of the present invention.

FIG. 19 schematically shows in perspective still other microphones 46A, 46B in addition to the microphone 45. The microphone 46A is positioned substantially centrally between the left and right roof rails 30A, 30B of the vehicle 10A and at a position facing the ear, on the compartment side of an occupant seated on a front seat, and the microphone 46B is positioned substantially centrally between the left and right roof rails 30A, 30B of the vehicle 10A and at a position facing the ear, on the compartment side of an occupant seated on a rear seat. Output signals from the microphones 46A, 46B are used as error signals.

The microphones 46A, 46B are thus positioned because the sound pressure level of noise in the passenger compartment centrally between the left and right roof rails 30A, 30B of the vehicle 10A and at the position facing the ear, on the compartment side of the occupant seated on the front seat is substantially equal to the sound pressure level of noise in the passenger compartment centrally between the left and right roof rails 30A, 30B of the vehicle 10A and at the position facing the ear, on the compartment side of the occupant seated on the rear seat. Since the microphones 46A, 46B are thus positioned centrally between the left and right roof rails 30A, 30B of the vehicle 10A and respectively at the position facing the ear, on the compartment side of the occupant seated on the front seat and at the position facing the ear, on the compartment side of the occupant seated on the rear seat, the active noise control system can attenuate noise in the passenger compartment at the ears on the compartment side of the occupants where the sound pressure of the noise is relatively high.

As described above, the active noise control system according to the second embodiment is capable of providing the same noise cancellation effect in the vicinity of the ears of occupants as the noise cancellation effect produced at the positions of microphones for confirming noise cancellation.

An active noise control system according to a third embodiment of the present invention will be described below.

Figure 20:
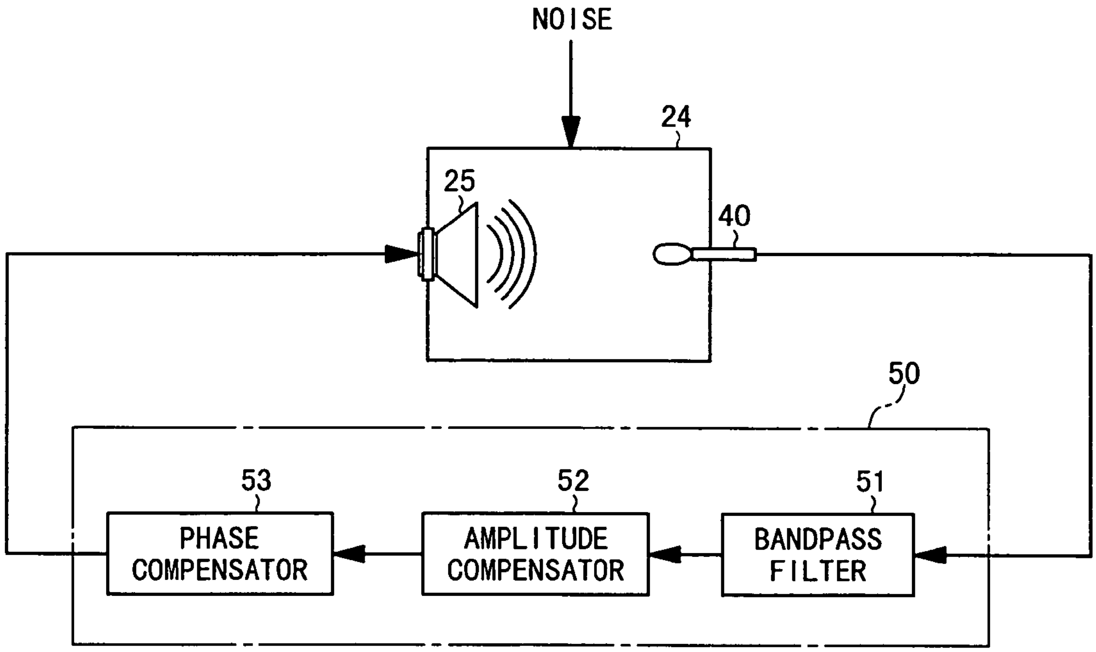
FIG. 20 is a block diagram of an active noise control system according to a third embodiment of the present invention.

FIG. 20 shows in block form the active noise control system according to the third embodiment of the present invention.

The active noise control system according to the third embodiment employs the microphone 40 in the active noise control system according to the first embodiment as a microphone for detecting noise, and has a feedback control circuit for controlling noise.

Specifically, the microphone 40 shown in FIG. 20 is used as a microphone for detecting noise, and an output signal from the microphone 40 is supplied to a feedback control circuit 50. An output signal from the feedback control circuit 50 is applied to drive the speaker 25 to cancel out noise in the passenger compartment 24.

The feedback control circuit 50 serves as an adjusting circuit for adjusting the amplitude and phase of the output signal from the microphone 40 based on the output signal from the microphone 40. The feedback control circuit 50 generates a cancellation signal which is of the same amplitude as, but out of phase to, noise at the microphone 40, and drives the speaker 25 with the cancellation signal.

Figure 21:
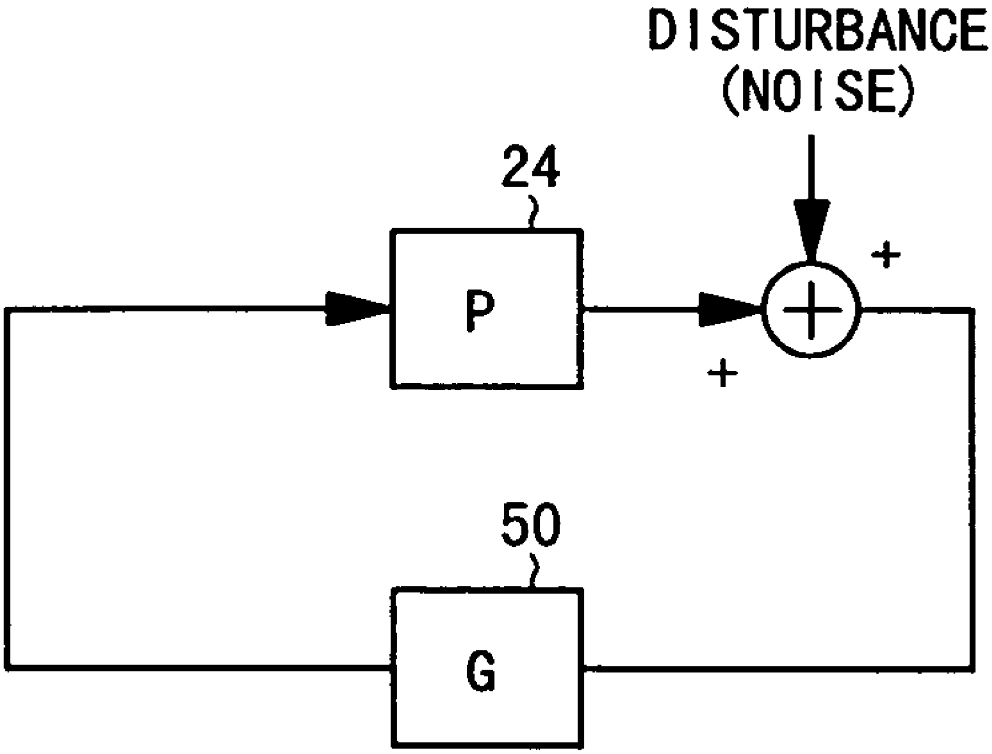
FIG. 21 is a block diagram illustrative of how the active noise control system according to the third embodiment of the present invention operates.

As shown in FIG. 21, the active noise control system according to the third embodiment, which includes the feedback control circuit 50, can be expressed by transfer functions P of the passenger compartment 24 including the speaker 25 and the microphone 40, and transfer functions G of the feedback control circuit 50. The feedback control circuit 50 operates to suppress disturbance (noise in the passenger compartment 24).

As shown in FIG. 20, the feedback control circuit 50 comprises a bandpass filter 51 for extracting noise in a certain frequency range, e.g., noise in a low frequency range including drumming noise, from the output signal from the microphone 40, an amplitude compensator 52 for compensating for the amplitude of an output signal from the bandpass filter 51 to generate an output signal having the same amplitude as the noise, and a phase compensator 53 for compensating for the phase of the output signal from the amplitude compensator 52 to generate an output signal that is out of phase to the noise. The output signal from the phase compensator 53 is applied to drive the speaker 25 to suppress the noise.

The amplitude compensator 52 and the phase compensator 53 serve as the adjusting circuit.

Figure 22:
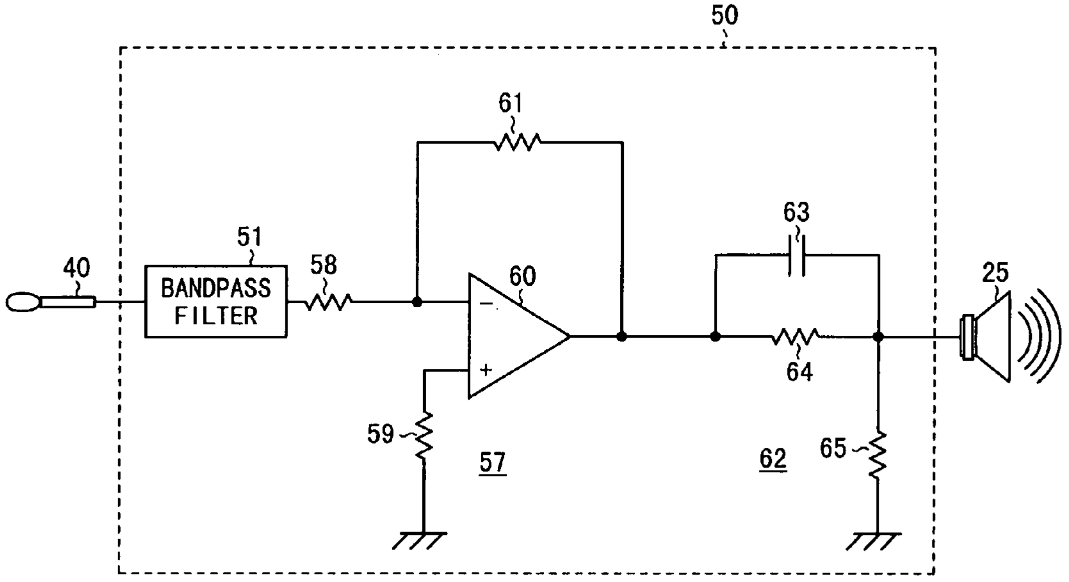
FIG. 22 is a circuit diagram of a feedback control circuit of the active noise control system according to the third embodiment of the present invention operates.

The feedback control circuit 50 will be described in more specific detail. As shown in FIG. 22, the feedback control circuit 50 comprises a bandpass filter 51 for extracting noise in a certain frequency range, e.g., noise in a low frequency range including drumming noise, from the output signal from the microphone 40, an inverting amplifier 57, operating as an amplitude compensator, for inversely amplifying an output signal from the bandpass filter 51, and a phase compensator 62 for advancing the phase of an output signal from the inverting amplifier 57. An output from the phase compensator 62 is applied to drive the speaker 25.

The inverting amplifier 57 comprises an operational amplifier 60, a resistor 58, a resistor 59, and a resistor 61. The phase compensator 62 comprises a capacitor 63, a resistor 64, and a resistor 65.

The output signal from the microphone 40 is inverted and amplified by the inverting amplifier 57 to the same amplitude as the noise at the microphone 40. The inverted and amplified signal is advanced in phase by the phase compensator 62, which outputs a signal which is of the same amplitude as, but out of phase to, the noise. The output signal from the phase compensator 62 is applied to drive the speaker 25 to eliminate output signal from the microphone 40 for thereby canceling out the noise in the passenger compartment 24.

In FIG. 22, the inverting amplifier 57 is employed in the feedback control circuit 50. However, the feedback control circuit 50 may have a noninverting amplifier insofar as the output signal from the feedback control circuit 50 is out of phase to the noise at the microphone 40. Though the phase compensator 62 comprises a first order passive phase lead compensator in the illustrated embodiment, the phase compensator 62 may comprise a second order passive phase lead compensator or an active phase compensator. Because the microphone 40 is positioned at the foremost position in the passenger compartment of an antinode in the primary or secondary acoustic normal mode of the passenger compartment 24, the microphone 40 produces an output signal indicative of detected noise at 40 Hz or 80 Hz. Based on the output signal indicative of detected noise at 40 Hz or 80 Hz, the extent of amplitude compensation of the amplitude compensator 52 and the extent of phase compensation of the phase compensator 53 are adjusted to suppress not only the noise at the microphone but also the noise in the low frequency range including drumming noise in the entire passenger compartment.

Specifically, the noise detected at 40 Hz and 80 Hz by the microphone 40 that is located at an antinode in the primary or secondary acoustic normal mode of the passenger compartment 24 behaves as a standing wave. The active noise control system according to the third embodiment operates to change the standing wave in the passenger compartment 24 in order to lower the sound pressure of the antinode of the standing wave where the microphone 40 is located. In some cases, the active noise control system can cancel out the standing wave in order to suppress the noise in the entire passenger compartment 24.

The active noise control system according to the third embodiment comprises the feedback control circuit 50 of simple construction which comprises the amplitude compensator 52 and the phase compensator 53 for noise cancellation. Therefore, the active noise control system may be smaller in size and more inexpensive than an active noise control system based on feed-forward control principles, and is less costly than a system for canceling out noise by adjusting the weight of a certain region of the vehicle body.

Figure 23:
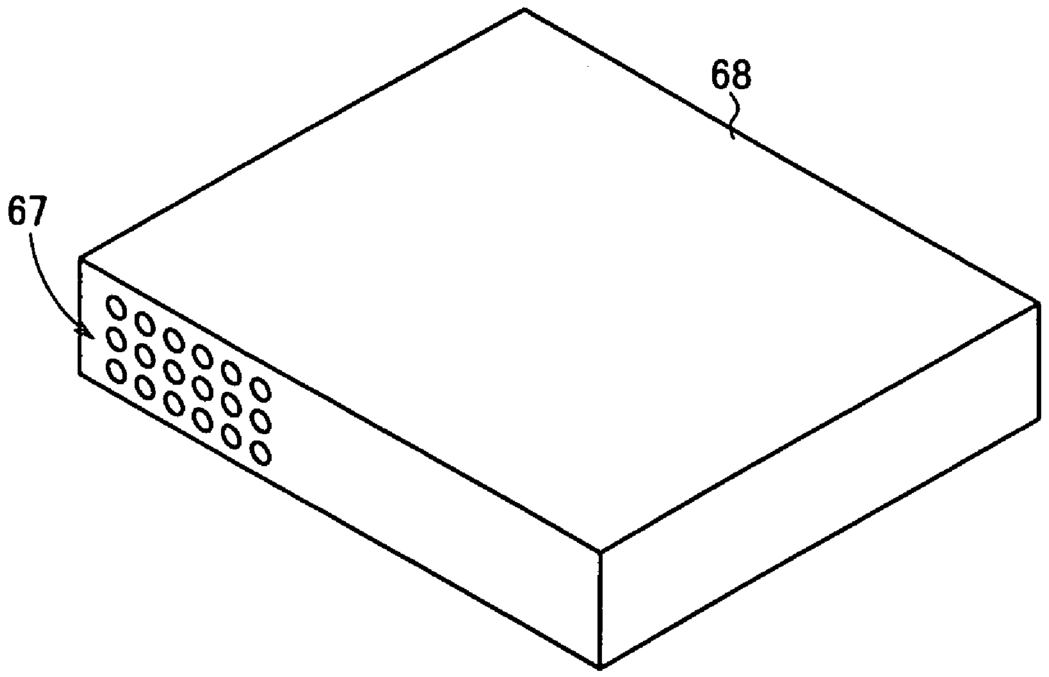
FIG. 23 is a perspective view of a storage box which stores the active noise control system according to the third embodiment of the present invention.
Figure 24:
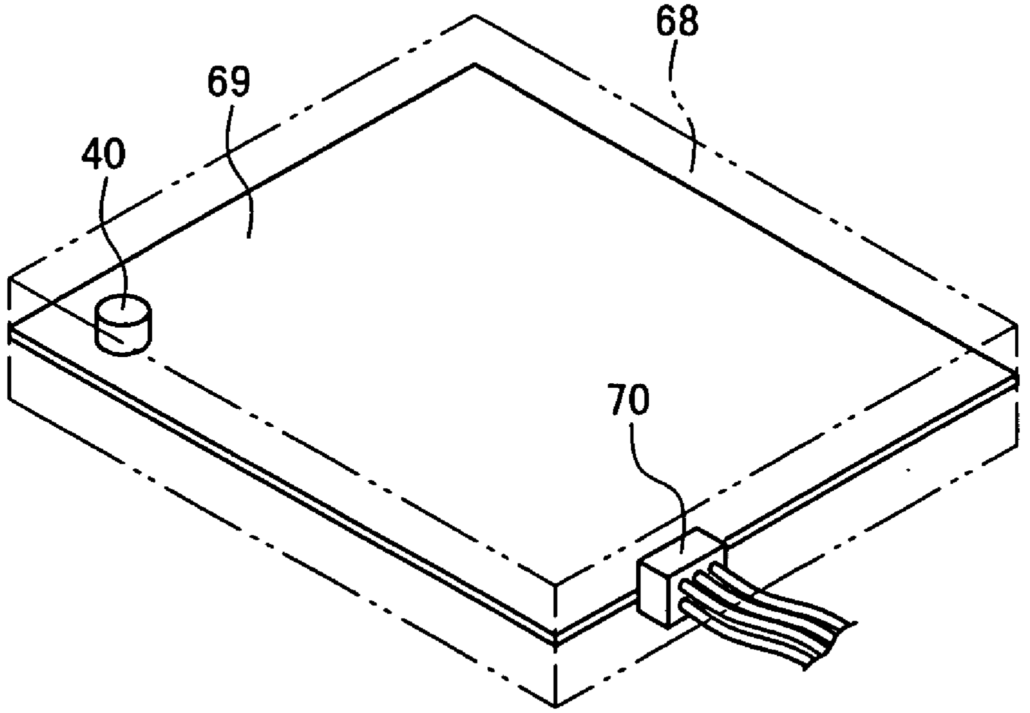
FIG. 24 is a perspective view showing a microphone and a circuit board in the storage box which stores the active noise control system according to the third embodiment of the present invention.
Figure 25:
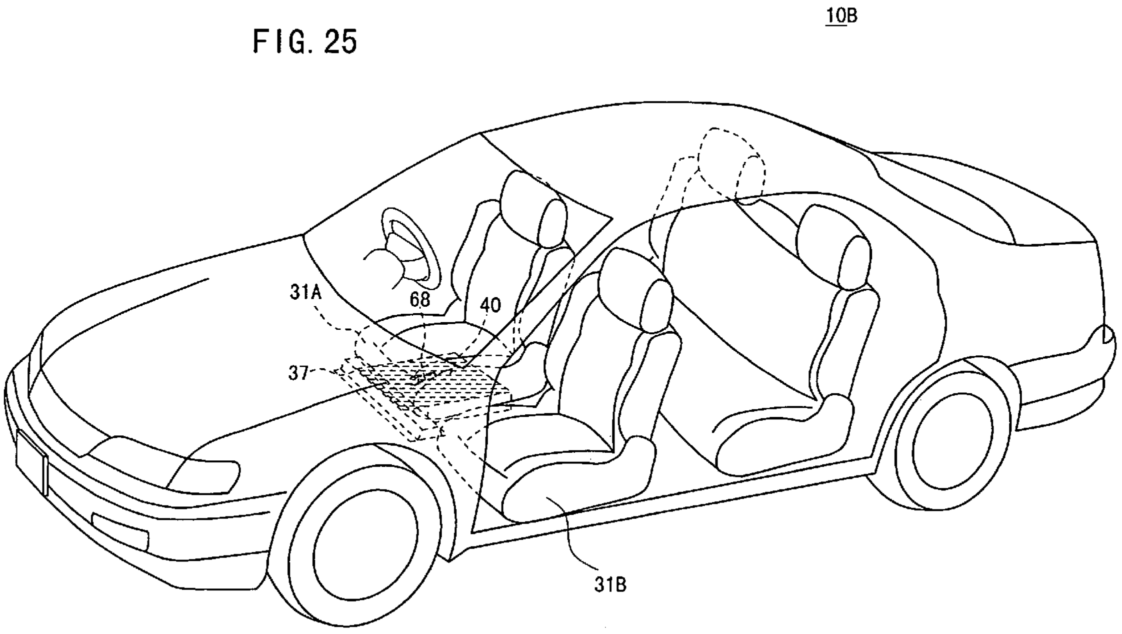
FIG. 25 is a schematic perspective view showing the position in which the active noise control system according to the third embodiment of the present invention is installed in a vehicle.
Figure 26:
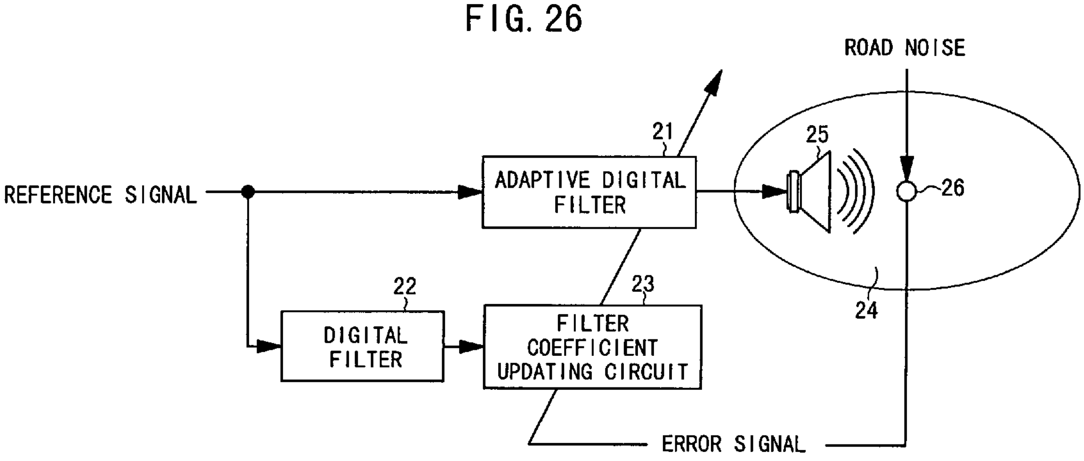
FIG. 26 is a block diagram of a conventional active noise control system.

The feedback control circuit 50 may be arranged in a small size and combined with the microphone 40. FIG. 23 shows a storage box 68 having noise passage holes 67 defined therein. As shown in FIG. 24, the feedback control circuit 50 and the microphone 40 combined therewith are installed on a circuit board 69, and housed in the storage box 68. The circuit board 69 has a connector 70 for connection to an external circuit. As shown in FIG. 25, the storage box 68 with the circuit board 69 placed therein is positioned beneath the base of the driver seat, i.e., the base of the front seat 31A, or the base of the front seat 31B, and fixed to a floor cross member 37 of a vehicle 10B. In FIG. 25, the doors of the vehicle 10B are omitted from illustration for a clearer presentation of the passenger compartment.

Since the storage box 68 is positioned beneath the base of the driver seat, i.e., the base of the front seat 31A, or the base of the front seat 31B, the storage box 68 cannot easily be touched by occupants, who are thus inhibited to touch the microphone 40. Because the microphone 40 and the feedback control circuit 50 are essentially integral with each other, the length of the microphone cord can be reduced, resulting in a reduced cost. Furthermore, the microphone 40 housed in the storage box 68 is prevented from being subject to an air flow that is produced when an occupant is seated on the front seat 31A or 31B.

As described above, the active noise control system according to the third embodiment is capable of canceling out noise in the passenger compartment based on low-frequency road noise and drumming noise with the simple arrangement that is composed of the microphone for detecting noise and the feedback control circuit.

Although certain preferred embodiments of the present invention have been shown and described in detail, it should be understood that various changes and modifications may be made therein without departing from the scope of the appended claims.

What is claimed is:

1. An active noise control circuit comprising:

feed-forward control means for being supplied with a reference signal highly correlated to noise from a noise source and generating a noise cancellation signal which is out of phase to noise in the passenger compartment of a vehicle with a fixed roof;

canceling sound generating means disposed in the passenger compartment for generating a noise canceling sound in response to the noise cancellation signal from said feed-forward control means;

a microphone disposed in the passenger compartment of the vehicle with the fixed roof, the microphone being centrally located on the fixed roof of the vehicle and at an antinode of an acoustic normal mode of the passenger compartment, for detecting said noise of which sound pressure level is high, and for generating the reference signal; and a noise cancellation-confirming microphone for confirming cancellation of the noise in the passenger compartment, and for generating an error signal;

wherein said feed-forward control means comprises means for lowering the levels of said error signal from said noise cancellation-confirming microphone with the noise cancellation signal; and wherein said noise cancellation-confirming microphone is positioned in a vicinity of ears of occupants seated in the passenger compartment.

2. An active noise control circuit according to claim 1, wherein said antinode of the acoustic normal mode of the passenger compartment comprises an antinode in a primary mode or a secondary mode in a longitudinal direction of the passenger compartment.

3. An active noise control circuit according to claim 1, wherein said noise cancellation-confirming microphone comprises a plurality of noise cancellation-confirming microphones being positioned respectively near laterally spaced roof rails of the vehicle in confronting relationship to the ears of occupants seated in the passenger compartment.

4. An active noise control circuit according to claim 1, wherein said noise cancellation-confirming microphone is positioned substantially centrally between laterally spaced roof rails of the vehicle in confronting relationship to the ear on the compartment side of an occupant seated in the passenger compartment.

5. An active noise control system according to claim 3 or 4, further comprising a microphone disposed near a central console in the passenger compartment.

6. The active noise control system according to claim 1, wherein frequency of said noise ranges from 20 to 120 Hz.

7. The active noise control system according to claim 1, wherein frequency of said noise ranges from 40 to 80 Hz.

8. An active noise control system comprising:

a microphone positioned in the passenger compartment of a vehicle having a fixed roof, the microphone being centrally located on the fixed roof of the vehicle at an antinode of a primary or secondary acoustic normal mode of the passenger compartment of the vehicle for detecting said noise of which sound pressure level is high and for generating an output signal;

canceling sound generating means disposed in the passenger compartment for generating a noise canceling sound;

a feedback control circuit for being supplied with the output signal from said microphone highly correlated to noise from a noise source and generating a noise cancellation signal which is out of phase to noise in the passenger compartment of the vehicle with the fixed roof for energizing said canceling sound generating means; and a storage box, wherein said microphone and said feedback control circuit are housed together in said storage box, said feedback control circuit having an adjusting circuit for adjusting the amplitude and phase between the canceling sound generating means and the microphone, based on a transfer characteristic from said microphone, to generate a noise cancellation signal which is of the same sound pressure as, but out of phase to, noise at the microphone.

9. An active noise control system according to claim 8, wherein said storage box is disposed beneath a front seat in the passenger compartment.

10. An active noise control system according to claim 8, wherein said storage box has holes defined therein for the passage of noise in the passenger compartment.

11. The active noise control system according to claim 8, wherein frequency of said noise ranges from 20 to 120 Hz.

12. The active noise control system according to claim 8, wherein frequency of said noise ranges from 40 to 80 Hz.

* * * * *